United States Patent [19]
Mulvihill et al.

[11] Patent Number: 5,403,734
[45] Date of Patent: Apr. 4, 1995

[54] T-PA WITH GROWTH FACTOR DOMAIN SUBSTITUTIONS

[75] Inventors: Eileen R Mulvihill; Patrick J. O'Hara, both of Seattle, Wash.

[73] Assignee: ZymoGenetics, Inc., Seattle, Wash.

[21] Appl. No.: 776,854

[22] Filed: Oct. 15, 1991

Related U.S. Application Data

[63] Continuation of Ser. No. 162,847, Mar. 2, 1988, abandoned, which is a continuation-in-part of Ser. No. 58,061, Jun. 4, 1987, abandoned.

[51] Int. Cl.⁶ .................. C12N 9/64; C12N 15/00; C12N 9/50
[52] U.S. Cl. .................. 435/226; 435/172.3; 435/212
[58] Field of Search .................. 735/212, 226, 320.1, 735/69.1, 70.1; 935/23, 27, 70, 73; 536/27

[56] References Cited
FOREIGN PATENT DOCUMENTS
093619 of 0000 European Pat. Off. ..... C12N 15/00

OTHER PUBLICATIONS

Appella et al., J. Biol. Chem., vol. 262, No. 10, pp. 4437–4440 (1987).
Gray et al., Nature, vol. 303, pp. 722–725 (1983).
Foster et al., Proc. Natl. Acad. Sci. USA, vol. 81, pp. 4766–4770, (1984).
Hagen et al., Proc. Natl. Acad. Sci. USA, vol. 83, pp. 2412–2416 (1986).
Beebe, Throwb. Res. 46: 245–254 (1987).
Hajjar et al., J. Clin. Invest. 80: 1712–1719 (1987).
Beebe et al., Blood 74: 2034–2037 (1989).
Fuchs, Blood 65: 539–544 (1985).
Blasi et al., J. Cell. Biol. 104: 801 (1987).
Webster's II new Riverside University Dictionary, p. 1129, Houghton Mifflin Co., Boston, Mass. 1984.

*Primary Examiner*—Richard A. Schwartz
*Assistant Examiner*—Nancy T. Vogel
*Attorney, Agent, or Firm*—Seed and Berry

[57] ABSTRACT

A plasminogen activator comprising a growth factor domain, a kringle domain and a serine protease domain is disclosed. The growth factor domain contains a plurality of substitutions of substantially consecutive amino acids as compared to the growth factor domain of native t-PA, the substitutions resulting in an increase in plasma half-life.

6 Claims, 20 Drawing Sheets

FIG. 1

```
           10                    30                        45
AAGCTTGGAT CCACC ATG GAT GCA ATG AAG AGA GGG CTC TGC TGT GTG CTG CTG CTG
                 MET Asp Ala MET Lys Arg Gly Leu Cys Cys Val Leu Leu Leu
                 -35             -30
    60                    75                     90                   105
TGT GGC GCC GTC TTC GTT TCG CCC AGC CAG GAA ATC CAT GCC CGA TTC AGA AGA
Cys Gly Ala Val Phe Val Ser Pro Ser Gln Glu Ile His Ala Arg Phe Arg Arg
        -20                                 -10
                120                   135                   150                   165
GGA GCC AGA TCT TAC CAA GTG ATC TGC AGA GAT GAA AAA ACG CAG ATG ATA TAC
Gly Ala Arg Ser Tyr Gln Val Ile Cys Arg Asp Glu Lys Thr Gln MET Ile Tyr
            1                                       10
                    180                   195                   210
CAG CAA CAT CAG TCA TGG CTG CGC CCT GTG CTC AGA AGC AAC CGG GTG GAA TAT
Gln Gln His Gln Ser Trp Leu Arg Pro Val Leu Arg Ser Asn Arg Val Glu Tyr
                20                                          30
    225                   240                   255                   270
TGC TGG TGC AAC AGT GGC AGG GCA CAG TGC CAC TCA GTG CCT GTC AAA AGT TGC
Cys Trp Cys Asn Ser Gly Arg Ala Gln Cys His Ser Val Pro Val Lys Ser Cys
                        40                                              50
            285                   300                   315
AGC GAG CCA AGG TGT TTC AAC GGG GGC ACC TGC CAG CAG GCC CTG TAC TTC TCA
Ser Glu Pro Arg Cys Phe Asn Gly Gly Thr Cys Gln Gln Ala Leu Tyr Phe Ser
                            60
330                   345                   360                   375
GAT TTC GTG TGC CAG TGC CCC GAA GGA TTT GCT GGG AAG TGC TGT GAA ATA GAT
Asp Phe Val Cys Gln Cys Pro Glu Gly Phe Ala Gly Lys Cys Cys Glu Ile Asp
70                                              80
        390                   405                   420                   435
ACC AGG GCC ACG TGC TAC GAG GAC CAG GGC ATC AGC TAC AGG GGC ACG TGG AGC
Thr Arg Ala Thr Cys Tyr Glu Asp Gln Gly Ile Ser Tyr Arg Gly Thr Trp Ser
            90                                      100
                    450                   465                   480
ACA GCG GAG AGT GGC GCC GAG TGC ACC AAC TGG AAC AGC AGC GCG TTG GCC CAG
Thr Ala Glu Ser Gly Ala Glu Cys Thr Asn Trp Asn Ser Ser Ala Leu Ala Gln
                110                                         120
    495                   510                   525                   540
AAG CCC TAC AGC GGG CGG AGG CCA GAC GCC ATC AGG CTG GGC CTG GGG AAC CAC
Lys Pro Tyr Ser Gly Arg Arg Pro Asp Ala Ile Arg Leu Gly Leu Gly Asn His
                        130                                             140
            555                   570                   585
AAC TAC TGC AGA AAC CCA GAT CGA GAC TCA AAG CCC TGG TGC TAC GTC TTT AAG
Asn Tyr Cys Arg Asn Pro Asp Arg Asp Ser Lys Pro Trp Cys Tyr Val Phe Lys
                            150
600                   615                   630                   645
GCG GGG AAG TAC AGC TCA GAG TTC TGC AGC ACC CCT GCC TGT TCT GAG GGA AAC
Ala Gly Lys Tyr Ser Ser Glu Phe Cys Ser Thr Pro Ala Cys Ser Glu Gly Asn
160                                             170
        660                   675                   690                   705
AGT GAC TGC TAC TTT GGG AAT GGG TCA GCC TAC CGT GGC ACG CAC AGC CTC ACC
Ser Asp Cys Tyr Phe Gly Asn Gly Ser Ala Tyr Arg Gly Thr His Ser Leu Thr
            180                                         190
```

FIG. 1A

```
                        720                       735                      750
GAG TCG GGT GCC TCC TGC CTC CCG TGG AAT TCC ATG ATC CTG ATA GGC AAG GTT
Glu Ser Gly Ala Ser Cys Leu Pro Trp Asn Ser MET Ile Leu Ile Gly Lys Val
                200                       780                       210
    765                       780                      795                     810
TAC ACA GCA CAG AAC CCC AGT GCC CAG GCA CTG GGC CTG GGC AAA CAT AAT TAC
Tyr Thr Ala Gln Asn Pro Ser Ala Gln Ala Leu Gly Leu Gly Lys His Asn Tyr
                        220                       840                       230
            825                       840                      855
TGC CGG AAT CCT GAT GGG GAT GCC AAG CCC TGG TGC CAC GTG CTG AAG AAC CGC
Cys Arg Asn Pro Asp Gly Asp Ala Lys Pro Trp Cys His Val Leu Lys Asn Arg
                                    240
870                       885                       900                      915
AGG CTG ACG TGG GAG TAC TGT GAT GTG CCC TCC TGC TCC ACC TGC GGC CTG AGA
Arg Leu Thr Trp Glu Tyr Cys Asp Val Pro Ser Cys Ser Thr Cys Gly Leu Arg
250                                                 260
        930                       945                      960                     975
CAG TAC AGC CAG CCT CAG TTT CGC ATC AAA GGA GGG CTC TTC GCC GAC ATC GCC
Gln Tyr Ser Gln Pro Gln Phe Arg Ile Lys Gly Gly Leu Phe Ala Asp Ile Ala
                270                                         280
                990                       1005                    1020
TCC CAC CCC TGG CAG GCT GCC ATC TTT GCC AAG CAC AGG AGG TCG CCC GGA GAG
Ser His Pro Trp Gln Ala Ala Ile Phe Ala Lys His Arg Arg Ser Pro Gly Glu
                        290                                         300
        1035                      1050                    1065                    1080
CGG TTC CTG TGC GGG GGC ATA CTC ATC AGC TCC TGC TGG ATT CTC TCT GCC GCC
Arg Phe Leu Cys Gly Gly Ile Leu Ile Ser Ser Cys Trp Ile Leu Ser Ala Ala
                                    310                                         320
            1095                      1110                    1125
CAC TGC TTC CAG GAG AGG TTT CCG CCC CAC CAC CTG ACG GTG ATC TTG GGC AGA
His Cys Phe Gln Glu Arg Phe Pro Pro His His Leu Thr Val Ile Leu Gly Arg
                                        330
1140                      1155                      1170                    1185
ACA TAC CGG GTG GTC CCT GGC GAG GAG GAG CAG AAA TTT GAA GTC GAA AAA TAC
Thr Tyr Arg Val Val Pro Gly Glu Glu Glu Gln Lys Phe Glu Val Glu Lys Tyr
340                                             350
            1200                      1215                    1230                    1245
ATT GTC CAT AAG GAA TTC GAT GAT GAC ACT TAC GAC AAT GAC ATT GCG CTG CTG
Ile Val His Lys Glu Phe Asp Asp Asp Thr Tyr Asp Asn Asp Ile Ala Leu Leu
                360                                         370
            1260                      1275                    1290
CAG CTG AAA TCG GAT TCG TCC CGC TGT GCC CAG GAG AGC AGC GTG GTC CGC ACT
Gln Leu Lys Ser Asp Ser Ser Arg Cys Ala Gln Glu Ser Ser Val Val Arg Thr
                        380                                         390
    1305                      1320                      1335                    1350
GTG TGC CTT CCC CCG GCG GAC CTG CAG CTG CCG GAC TGG ACG GAG TGT GAG CTC
Val Cys Leu Pro Pro Ala Asp Leu Gln Leu Pro Asp Trp Thr Glu Cys Glu Leu
                                    400                                         410
                1365                      1380                    1395
TCC GGC TAC GGC AAG CAT GAG GCC TTG TCT CCT TTC TAT TCG GAG CGG CTG AAG
Ser Gly Tyr Gly Lys His Glu Ala Leu Ser Pro Phe Tyr Ser Glu Arg Leu Lys
                                            420
```

```
1410              1425                    1440                     1425
GAG GCT CAT GTC AGA CTG TAC CCA TCC AGC CGC TGC ACA TCA CAA CAT TTA CTT
Glu Ala His Val Arg Leu Tyr Pro Ser Ser Arg Cys Thr Ser Gln His Leu Leu
430                                      440
         1470                    1485                  1500                  1515
AAC AGA ACA GTC ACC GAC AAC ATG CTG TGT GCT GGA GAC ACT CGG AGC GGC GGG
Asn Arg Thr Val Thr Asp Asn MET Leu Cys Ala Gly Asp Thr Arg Ser Gly Gly
        450                                           460
              1530                  1545                   1560
CCC CAG GCA AAC TTG CAC GAC GCC TGC CAG GGC GAT TCG GGA GGC CCC CTG GTG
Pro Gln Ala Asn Leu His Asp Ala Cys Gln Gly Asp Ser Gly Gly Pro Leu Val
                 470                                            480
     1575                    1590                   1605                 1620
TGT CTG AAC GAT GGC CGC ATG ACT TTG GTG GGC ATC ATC AGC TGG GGC CTG GGC
Cys Leu Asn Asp Gly Arg MET Thr Leu Val Gly Ile Ile Ser Trp Gly Leu Gly
                                490                                      500
           1635                    1650                  1665
TGT GGA CAG AAG GAT GTC CCG GGT GTG TAC ACA AAG GTT ACC AAC TAC CTA GAC
Cys Gly Gln Lys Asp Val Pro Gly Val Tyr Thr Lys Val Thr Asn Tyr Leu Asp
                                    510
1680                1695                  1714       1724       1734
TGG ATT CGT GAC AAC ATG CGA CCG TGA CCAGGAACAC CCGACTCCTC AAAAGCAAAT
Trp Ile Arg Asp Asn MET Arg Pro
520                             527

1740
GAGATC
```

```
        KpnI                                              NsiI
         |                                                 |
                    ZC1351                                        ZC1353
SerValProValLysSerCysSerGluProArgCysPheAsnGlyGlyThrCysMetGluGlyAsnHis
TCGGTACCTGTTAAATCTTGTTCTGAACCTAGATGTTTTAATGGAGGAACATGCATGGAAGGAAATCAT
AGCCATGGACAATTTAGAACAAGACTTGGATCTACAAAATTACCTCCTTGTACGTACCTTCCTTTAGTA
                    ZC1352                                        ZC1354
```

```
                                                              XhoI
                              ZC1355                            |
LeuAlaAsnPheValCysGlnCysProGluGlyPheAlaGlyLysSerCysGluIleAspThrArgAla
CTTGCTAATTTTGTTTGTCAATGTCCTGAAGGATTTGCTGGAAAATCTTGTGAAATTGATACTCGAGCT
GAACGATTAAAACAAACAGTTACAGGACTTCCTAAACGACCTTTTAGAACACTTTAACTATGAGCTCGA
                              ZC1356
```

2.

```
        KpnI
         |
                    ZC1357                                        ZC1359
SerValProValLysSerCysGluSerAsnProCysLeuAsnGlyGlySerCysLysAspAspIleAsn
TCGGTACCTGTTAAATCTTGTGAATCTAATCCTTGTCTTAATGGAGGATCTTGTAAAGATGATATTAAT
AGCCATGGACAATTTAGAACACTTAGATTAGGAACAGAATTACCTCCTAGAACATTTCTACTATAATTA
                    ZC1358                                        ZC1360
```

```
    NdeI                                                      XhoI
     |                        ZC1361                            |
SerTyrGluCysTrpCysProPheGlyPheGluGlyLysAsnCysGluIleAspThrArgAla
TCATATGAATGTTGGTGTCCTTTTGGATTTGAAGGAAAAAATTGTGAAATTGATACTCGAGCT
AGTATACTTACAACCACAGGAAAACCTAAACTTCCTTTTTTAACACTTTAACTATGAGCTCGA
                              ZC1362
```

3.

```
        KpnI
         |
                    ZC1457
SerValProValLysSerCysAlaSerSerProCysGlnAsnGlyGlySerCysLysAspGlnLeuGln
TCGGTACCTGTTAAATCTTGTGCTTCTTCTCCTTGTCAAAATGGAGGATCTTGTAAAGATCAACTTCAA
AGCCATGGACAATTTAGAACACGAAGAAGAGGAACAGTTTTACCTCCTAGAACATTTCTAGTTGAAGTT
                    ZC1458
```

```
    NdeI                                                      XhoI
     |                        ZC1459                            |
SerTyrIleCysPheCysLeuProAlaPheGluGlyArgAsnCysGluIleAspThrArgAla
TCTTACATATGTTTTTGTCTTCCTGCTTTTGAAGGAAGAAATTGTGAAATTGATACTCGAGCT
AGAATGTATACAAAAACAGAAGGACGAAAACTTCCTTCTTTAACACTTTAACTATGAGCTCGA
                              ZC1460
```

4.

```
    AflIII
     |                ZC1363
       ThrCysGlnGlnAlaLeuTyrPheSerAspPheValCysGlnCysPro
        ACATGTCAACAAGCTCTTTATTTTTCTGATTTTGTTTGTCAATGTCCT
        CCTCCTTGTACAGTTGTTCGAGAAATAAAAAGACTAAAACAAACAGTT
                              ZC1364
```

*FIG. 6*

```
                                    Cys Lys Thr Gly Asp Gly Lys Asn Tyr Arg Gly Thr Met Ser
                                    TGC AAG ACC GGT GAT GGT AAA AAC TAC CGA GGT ACC ATG TCC

Lys Thr Lys Asn Gly Ile Thr Cys Gln Lys Trp Ser Ser Thr Ser Pro His Arg Pro Arg
AAG ACC AAA AAC GGT ATT ACA TGT CAG AAA TGG TCA TCT ACT AGT CCA CAC CGG CCG CGG

Phe Ser Pro Ala Thr His Pro Ser Glu Gly Leu Glu Glu Asn Tyr Cys Arg Asn Pro Asp
TTT TCT CCA GCT ACC CAT CCA TCT GAA GGC CTG GAA GAG AAT TAC TGT AGG AAT CCA GAT

Asn Asp Pro Gln Gly Pro Trp Cys Tyr Thr Thr Asp Pro Glu Lys Arg Tyr Asp Tyr Cys
AAC GAT CCT CAG GGT CCC TGG TGT TAC ACC ACA GAC CCC GAG AAG AGG TAC GAC TAC TGC

Asp Ile Leu Glu Cys
GAT ATC CTG GAA TGC
```

FIG. 7

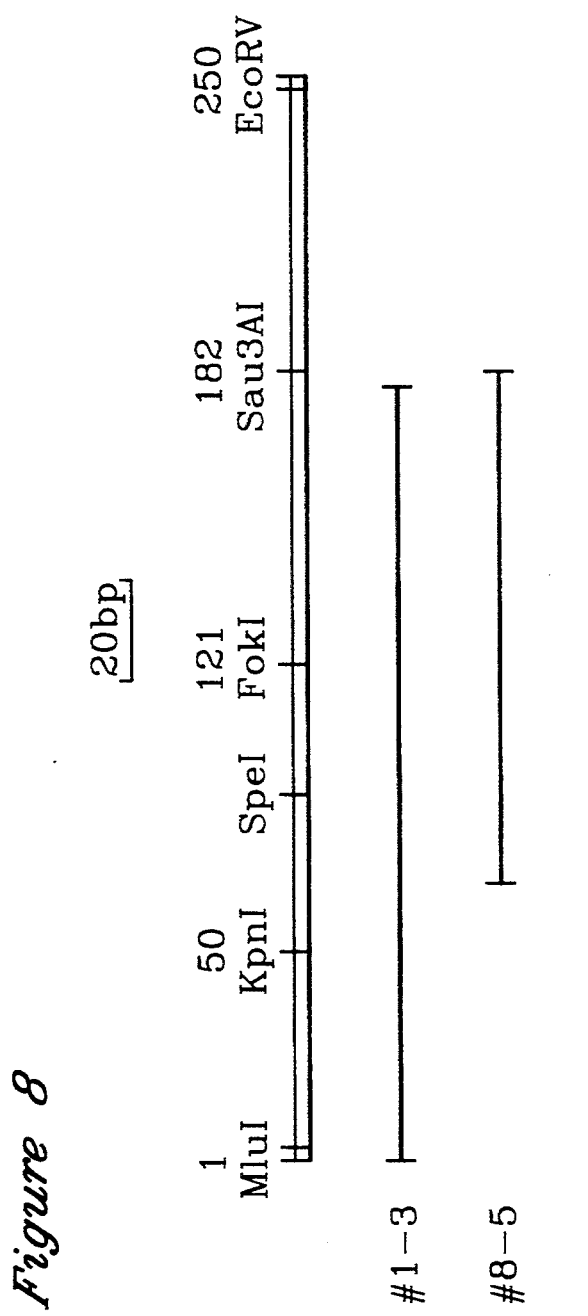

FIG. 15A

```
TPA:     CS-E---PR--------CFNGGT--------CQQALYFSD----FVCQC-PEG---F----A-GKCC
Urokh:   C-----D----------CLNGGT--------CVSNKYFSNI--IIW-CNC-P---KK-F----G-GQHC
Urokp:   C----------------GCLNGGK-------CVSYKYFSNI-QR--CSC-P---KK-F----Q-GEHC
Urokm:   C----------------GCQNGGV-------CVSYKYFSRI-RR--CSC-P---RK-F----Q-GEHC
F7-4h:   CA--SSP----------CQNGGS--------CKDQLQS-----YICFCLPA---F------EGRNC
F9-4h:   C---ESNP---------CLNGGS--------CKDDINS-----YECWC-PFG---F------EGKNC
F9-4b:   C---ESNP---------CLNGGM--------CKDDINS-----YECWCQ-AG---F------EGTNC
F10-4h:  C---ETSP---------CQNQGK--------CKDGLGE-----YTCTCL-EG---F------EGKNC
F10-4b:  C---EGHP---------CLNQGH--------CKDGIGD-----YTCTCA-EG---F------EGKNC
PS-4Ah:  CS----PL---P-----CNEDGYMS------CKDGKAS-----FTCTCKP-G---W------Q-GEKC
PS-4Ab:  CN----PL---P-----CNEDGFMT------CKDGQAT-----FTCICK-SG---W------Q-GEKC
PZ-4b:   CA--SQP----------CLNNGS--------CQDSIRG-----YACTCAP-G---Y------EGPNC
EGFh:    C---PLSH----DGYCLHDGV----------CMYIEALD----KYACNCV-VG---YIG----E-R-C
EGFm:    C---PSSY----DGYCLNGGV----------CMHIESLDS---YTCNCV-IG---YSG----D-R-C
TGFah:   C-----PDSHTQF----CFHGT---------CRFLVQED----KPA-CVCH-SG---YVGA----R-C
TGFar:   C-----PDSHTQY----CFHGT---------CRFLVQEE----KPA-CVCH-SG---YVGV----R-C
TGFlr:   C-----PDSHTQY----CFHGT---------CRFLVQEE----KPA-CVCH-SG---YVGV----R-C
C9:      C-----IIT--------CQNGGTVILMDGKCL-----------------CAC-PF-K---F----EGIAC
```

FIG. 15B

```
F7-5:      CVNE--------NGGC-EQ-Y------CSDHTGT----KRS-CRCH-EG----YSLLADGVSC
F9-5h:     CN-IK-------NGRC-EQ-F------CKNSADN----KVV-CSCT-EG----YRLAENQKSC
F9-5b:     CS-IK-------NGRC-KQ-F------CKRDTDN----KVV-CSCT-DG----YRLAEDQKSC
F10-5h:    CSLD--------NGDC-DQ-F------CIIEEQNS----VV--CSCA-RG----YTLADNGKAC
F10-5b:    CSLD--------NGGC-DQ-F------CREERSE-----VR--CSCA-HG----YVLGDDSKSC
PC-5h:     CSLD--------NGGCTH--Y------CLEEVGW-----RR--CSCAP-G----YKLGDDLLQC
PC-5b:     CSAE--------NGGCAH--Y------CMEEEG------RRH-CSCAP-G----YRLEDDHQLC
PS-5Ah:    CK-D--PSNI--NGGC-SQI-------CDNTPGS-----YHCSCK-NG----FVMLSNKKDC
PS-5Ab:    CK-D--PVNI--NGGC-SQI-------CENTPGS-----YHCSCK-NG----FVMLSNKKDC
EGFr1m:    CATQ--------NHGCTLG--------CENTPGS-----YHCTC-PTG----FVLLPDGKQC
LDLrAh:    C-----------LDN--NGGCSHV---CNDLKIG-----YECLC-PDG----FQLVA-QRRC
LDLrArb:   C-----------MRG--NGGCSHT---CFDLRIG-----HECHC-PKG----YRLV-DQRRC
EGFr3m:    CSS----PD---NGGCSQI--------CLPLRPGS----WECDCFP-G----YDLQSDRKSC
EGFr3h:    CSS----PD---NGGCSQL--------CVPLSPVS----WECDCFP-G----YDLQLDEKSC
EGFr4m:    CLYR--------NGGCEHI--------CQESLGTA----R---CLCR-EG---FVKAWDGKMC
EGFr4h:    CLYQ--------NGGCEHI--------CKKRLGTA----W---CSCR-EG---FMKASDGKTC
LDLrCh:    C--ERTTL--S-NGGCNYL--------CLPAPQINPHSPKFTCAC-PDG----MLLARDMRSC
LDLrCrb:   C--EKTAL--P-NGGCQYL--------CLPAPQINSHSPKFTCAC-PDG----TLLAADMRSC
EGFr5m:    CG----------PGGCGSHAR------CVSDGETAE---------CQCL-KG----F--ARDGNLC
```

FIG. 15C

```
PC-4h:    CLVL---PLEHPCASLCCGHGT-------------CIDGIGS-------FSCDCR-SG---W----EGRFC
PC-4b:    CE-DR-PSGSPCDLPCCGRGK-------------CIDGLGG-------FRCDCA-EG---W----EGRFC
PS-4Bh:   CS-LK-PSI--------CGTAV------------CKNILGD-------FECEC-PEGYR-YNLKS--KSC
PS-4Bb:   CV-LK-PSI--------CGTAV------------CKNIPGD-------FECECA-EGYK-YNPVS--KSC
PS-5Bh:   CS-E----NM-------C-AQL------------CVNYPGG-------HTCYCD--GKKGFKLAQDQKSC
PS-5Bb:   CA-E----NL-------C-AQL------------CVNYPGG-------YSCYCD--GKKGFKLAQDQKSC
EGFr2m:   C-------PGNVSK----CSHG------------CVLTSDGP----R--CIC-PAG---SVLGRDGKTC
EGFr2h:   C-------PRNVSE----CSHD------------CVLTSEGPL-----CFC-PEG---SVLERDGKTC
LDLrBh:   CQ--D---PDT------CSQL------------CVNLEGG-------YKCQCE-EG---FQLDPHTKAC
LDLrBrb:  CE--D---PDI------CSQL------------CVNLAGS-------YKCECR-AG---FQLDPHSQAC
EGFr6m:   CV------LARSD----CPSTSSR----------CINTEGG-------YVCRCS-EG---YEG--DGISC
EGFr7m:   C---QR--GAHN-----CAENAA-----------CTNTEGG-------YNCTCA--GR---PSSP-GRSC
```

ZC1351                            27
CTG TTA AAT CTT GTT CTG AAC CTA GAT GTT TTA ATG GAG GA

ZC1352                            27
ATT AAA ACA TCT AGG TTC AGA ACA AGA TTT AAC AGG TAC

ZC1353                            27
ACA TGC ATG GAA GGA AAT CAT CTT GCT AAT TTT GTT TGT CAA TGT
CCT

ZC1354                            27
TTG ACA AAC AAA ATT AGC AAG ATG ATT TCC TTC CAT GCA TGT TCC
TCC

ZC1355                            27
GAA GGA TTT GCT GGA AAA TCT TGT GAA ATT GAT AC

FIG. 16

ZC1356                            27
TCG AGT ATC AAT TTC ACA AGA TTT TCC AGC AAA TCC TTC AGG ACA

ZC1357                            27
CTG TTA AAT CTT GTG AAT CTA ATC CTT GTC TTA ATG GAG GA

ZC1358                            27
ATT AAG ACA AGG ATT AGA TTC ACA AGA TTT AAC AGG TAC

ZC1359                            27
TCT TGT AAA GAT GAT ATT AAT TCA TAT GAA TGT TGG TGT CCT

ZC1360                            27
CCA ACA TTC ATA TGA ATT AAT ATC ATC TTT ACA AGA TCC TCC

ZC1361                            27
TTT GGA TTT GAA GGA AAA AAT TGT GAA ATT GAT AC

ZC1362                            27
TCG AGT ATC AAT TTC ACA ATT TTT TCC TTC AAA TCC AAA AGG ACA

ZC1363                            27
ACA TGT CAA CAA GCT CTT TAT TTT TCT GAT TTT GTT TGT CAA TGT
CCT

ZC1364                            27
TTG ACA AAC AAA ATC AGA AAA ATA AAG AGC TTG TTG ACA TGT TCC
TCC

ZC1457
TCG GTA CCT GTT AAA TCT TGT GCT TCT TCT CCT TGT CAA AAT GGA
GGA TCT TGT AAA GAT CAA CTT CAA

ZC1458
AGC CAT GGA CAA TTT AGA ACA CGA AGA AGA GGA ACA GTT TTA CCT
CCT AGA ACA TTT CTA GTT GAA GTT

ZC1459
TCT TAC ATA TGT TTT TGT CTT CCT GCT TTT GAA GGA AGA AAT TGT
GAA ATT GAT ACT CGA GCT

ZC1460
AGA ATG TAT ACA AAA ACA GAA GGA CGA AAA CTT CCT TCT TTA ACA
CTT TAA CTA TGA GCT CGA

T-PA WITH GROWTH FACTOR DOMAIN SUBSTITUTIONS

CROSS-REFERENCE TO RELATED APPLICATION

This application is a continuation-in-part of U.S. application Ser. No. 07/162,847, filed Mar. 2, 1988, now abandoned, which is a continuation-in-part of Ser. No. 07/058,061, filed Jun. 4, 1987, now abandoned.

TECHNICAL FIELD

The present invention relates to fibrinolytic agents, methods for their production, and pharmaceutical compositions containing them. More specifically, it relates to tissue plasminogen activator analogs having a modified growth factor domain.

BACKGROUND OF THE INVENTION

Hemostasis is maintained by a complex interplay of a variety of enzymes. Clotting factors interact in a "cascade" of activation steps which eventually leads to the formation of a fibrin clot. Subsequent degradation of the fibrin clot is accomplished by the fibrinolytic system, which involves the serine protease plasmin, a proteolytic enzyme which breaks down fibrin. Plasmin is a broad spectrum protease which also cleaves certain coagulation factors, thereby inactivating them. Production of plasmin from its inactive precursor, plasminogen, is mediated by tissue plasminogen activator (t-PA), a fibrin-specific serine protease which is believed to be the physiological vascular activator of plasminogen. Urokinase-type plasminogen activator (u-PA) is another member of the class of plasminogen activators characterized as serine proteases. t-PA and u-PA are functionally and immunologically distinguishable. If the normal hemostatic system becomes upset, clots may form at inappropriate times and places, leading to myocardial infarction, deep vein thrombosis, pulmonary embolism and stroke. Tissue damage resulting from these conditions may result in death or serious disability.

t-PA normally circulates as a single polypeptide chain of $M_r=72,000$ daltons, which is converted to a two-chain form by cleavage of a peptide bond between amino acids 275 (Arg) and 276 (Ile). The heavy chain of t-PA (two variants of $M_r$ 40,000 and 37,000) is derived from the amino-terminus, while the light chain ($M_r$ 33,000) is derived from the carboxy-terminal end of the t-PA molecule. This cleavage is catalyzed by trypsin or plasmin, and is accompanied by an increase in activity, as measured using synthetic substrates, and by an increase in fibrinolytic activity. Single-chain t-PA becomes active upon binding to fibrin, probably due to a conformational change in the activator induced by binding to fibrin. Cleavage to the two-chain form may be associated with rapid clearance of t-PA from the bloodstream, but conflicting reports on this have been published (see Wallen et al., *Eur. J. Biochem.* 132:681–686, 1983), and the clearance mechanism is poorly understood.

A two-dimensional model of the potential precursor t-PA protein has been established (Ny et al., *Proc. Natl. Acad. Sci. USA* 81:5355–5359, 1984). From this model, it was determined that the heavy chain contains two triple disulfide structures known as "kringles." Similar kringle structures also occur in prothrombin, plasminogen and urokinase, and are believed to be important for binding to fibrin (Ny et al., ibid.). The second kringle (K2) of t-PA is believed to have a higher affinity for fibrin than the first kringle (K1) (Ichinose, Takio and Fujikawa, *J. Clin. Invest.* 78:163–169, 1986; Verheijen et al., *EMBO J.* 5:3525–3530, 986).

In addition, the heavy chain of t-PA contains a "growth factor" domain, a triple disulfide-bonded structure which has homology to epidermal growth factor and to similar domains in protein C, factor VII, factor IX and factor X. The growth factor domain of native t-PA encompasses approximately amino acids 48–90.

The heavy chain of t-PA also contains a "finger" domain that is homologous to the finger domains of fibro-nectin. Fibronectin exhibits a variety of biological activities, including fibrin binding; its fibrin-binding activity has been correlated to four or five of its nine finger domains.

The light chain of t-PA contains the active site for serine protease activity (the serine protease domain), which is highly homologous to the active sites of other serine proteases.

The precursor form of t-PA additionally comprises a pre-region followed downstream by a pro-region, which are collectively referred to as the "pre-pro" region. The pre-region contains a signal peptide which is important for secretion of t-PA by vascular endothelial cells (Ny et al., ibid.). The pre sequence is believed responsible for secretion of t-PA into the lumen of the endoplasmic reticulum, a necessary step in extracellular secretion. The pro sequence is believed to be cleaved from the t-PA molecule following transport from the endoplasmic reticulum to the Golgi apparatus.

The use of t-PA for fibrinolysis in animal and human subjects has highlighted several shortcomings of the native molecule. The half-life of t-PA in vivo has been shown to be as short as three minutes in humans (Nilsson et al., *Scand. J. Haematol.* 33:49–53, 1984). Injected t-PA is rapidly cleared by the liver, and, within 30 minutes, most of the injected material is metabolized to low molecular weight forms. This short half-life may result in a need for high therapeutic dosages. Typically, native t-PA is administered at a dose of 30 to 150 mg per patient, and the low solubility of the protein necessitates prolonged infusion. Fuchs et al. (*Blood* 65:539–544, 1985) concluded that infused t-PA is cleared by the liver in a process independent of the proteolytic site and that infused t-PA will not accumulate in the body; that is, the clearance mechanism cannot be saturated. Furthermore, doses of t-PA sufficient to lyse coronary thrombi are far larger than normal physiological levels, and may cause activation of plasminogen throughout the body, leading to systemic degradation of fibrinogen (Sherry, ibid.), which results in dangerous bleeding episodes.

Various workers have modified t-PA in attempts to enhance its clinical suitability. Rosa and Rosa (International Patent Application WO 86/01538) modified the Lys at position 277 of t-PA to stabilize the single-chain form of t-PA. Ile (277) t-PA produced in *E. coli* was found to be less active as a single-chain molecule, as compared to native t-PA. Wallen et al. (ibid.) postulated that the lysine residue at position 277 may be responsible for the proteolytic activity of single-chain t-PA. Heyneker and Vehar (published British Patent Application 2,173,804) disclose amino acid substitutions around the cleavage site of t-PA. A variant t-PA comprising Glu at position 275 was shown to have greater specific activity as compared to native t-PA. This variant t-PA also formed fewer complexes with t-PA inhibitor. The single-chain form was also shown to have greater affinity for fibrin than the two-chain form. Robinson (WO 84/01786) used enzymatic means to remove carbohydrate side chains from t-PA to increase plasma half-life. Lau et al. (*Bio/Technology* 5953, 1987) disclose a t-PA variant lacking carbohydrate at position 451. Van Zonneveld et al. (*Proc. Natl. Acad. Sci. USA* 83:4670–4674, 1986) disclose modified forms of t-PA wherein portions of the heavy chain have been deleted. Robinson et al. (EP 207,589 Al) disclose mutant forms of t-PA in which the growth factor domain has been deleted or otherwise modified. Larsen et al. (WO 87/04722) disclose t-PA-like proteins with amino acid substitutions and/or deletions. Ehrlich et al. (*Fibrinolysis* 1:75, 1987) disclose a recombinant t-PA molecule lacking the kringle domains. However, these variant forms of t-PA do not fully overcome the problems associated with the native protein.

There remains a need in the art for a plasminogen-activating protein with a longer half-life and specificity for fibrin. The present invention fulfills this need by providing novel derivatives of tissue plasminogen activator in which the growth factor domain has been structurally altered. The t-PA analogs described herein provide significant advantages over native t-PA as therapeutic fibrinolytic agents by permitting the use of much smaller doses, thus overcoming the problems of low solubility of native t-PA and potentially permitting administration by injection rather than infusion. Through the use of recombinant DNA technology, a consistent and homogeneous source of these proteins is provided. The proteins can be utilized to lyse existing clots in heart attack and stroke victims and in others where the need to lyse or suppress the formation of fibrin matrices is therapeutically desirable.

DISCLOSURE OF THE INVENTION

Briefly stated, the present invention discloses a plasminogen activator comprising a growth factor domain, a kringle domain and a serine protease domain, the growth factor domain containing a plurality of substitutions of substantially consecutive amino acids as compared to the growth factor domain of native. t-PA, the substitutions resulting in an increase in plasma half-life. For purposes of the present invention, the phrase "plurality of substitutions" is defined as four or more substitutions. These substantially consecutive amino acid substitutions may be made in more than one region of the growth factor domain. The growth factor domain may comprise an amino acid sequence of a protein such as factor VII, factor IX, protein C or epidermal growth factor. Within preferred embodiments, the growth factor domain comprises the amino acid sequence of a growth factor domain of any of fragments A-N as shown in FIG. 5. The plasminogen activator may also contain an amino acid substitution at the position corresponding to Cys (83) of native t-PA. The kringle domain may be the K1, K4 or K5 kringle of plasminogen. In selected embodiments, the plasminogen activator may contain two kringle domains, at least one of which lacks carbohydrate.

DNA constructs comprising a DNA sequence encoding a plasminogen activator comprising a growth factor domain, a kringle domain and a serine protease domain, wherein the growth factor domain contains a plurality of substitutions of substantially consecutive amino acids as compared to the growth factor domain of native t-PA, the substitutions resulting in an increase in plasma half-life, are also disclosed. Expression vectors comprising a transcriptional promoter operably linked to such a DNA sequence as well as host cells transfected or transformed with such an expression vector are also disclosed. Preferred host cells in this regard are cultured mammalian cells, such as tk⁻BHK cells.

Within yet another aspect of the present invention, a method for producing a plasminogen activator is disclosed. The method generally comprises (a) transfecting or transforming host cells with an expression vector comprising a transcriptional promoter operably linked to a DNA sequence encoding a plasminogen activator comprising a growth factor domain, a kringle domain and a serine protease domain, wherein the growth factor domain contains a plurality of substitutions of substantially consecutive amino acids as compared to the growth factor domain of native t-PA, the substitutions resulting in an increase in plasma half-life; (b) growing the host cells in an appropriate medium; and (c) isolating the plasminogen activator.

Within another aspect of the present invention, pharmaceutical compositions comprising the plasminogen activators disclosed above in combination with a physiologically acceptable carrier or diluent are also disclosed.

These and other aspects of the the present invention will become evident upon reference to the following detailed description and attached drawings.

BRIEF DESCRIPTION OF THE DRAWINGS

FIGS. 1A, and 1B illustrate the entire t-PA coding sequence constructed from cDNA and synthesized oligonucleotides, together with the amino acid sequence of the encoded protein. Numbers above the lines refer to nucleotide position and numbers below the lines refer to amino acid position.

FIG. 6 illustrates the amino acid sequences of representative growth factor domain sequences and the oligonucleotides encoding those sequences. Sequence 1, made up of oligonucleotides ZC 1351–ZC 1356, corresponds to substitution A shown in FIG. 5. Sequence 2 ( ZC 1357–ZC 1362) corresponds to substitution B of FIG. 5. Sequence 3 (ZC 1457–ZC 1460) corresponds to substitution F of FIG. 5. Sequence 4 (ZC 1362–ZC 1364) is a portion of the native t-PA growth factor domain. Lines indicate oligonucleotide boundaries.

FIG. 7 illustrates the amino acid sequence of the K1 domain of plasminogen and the DNA sequence encoding it.

FIG. 8 shows partial restriction maps of clones #1-3 and #8-5, which encode portions of the K1 kringle domain of plasminogen.

FIGS. 15A, B and C depict a comparison of the amino acid sequences of growth factor domains of a variety of selected proteins. The sequences are identified as follows: TPA, native tissue plasminogen activator; Urok, urokinase; F7, factor VII; F9, factor IX; F10, factor X; PS, protein S; PZ, protein Z; EGF, epidermal growth factor; TGFa, transforming growth factor alpha; TGFIr, transforming growth factor type I (rat); C9, complement factor 9; LDLr, low density lipoprotein receptor; EGFr, EGF receptor; PC, protein C. Other designations are h, human; p, porcine; m, mouse; b, bovine; and rb, rabbit. For factors VII, IX, X and proteins C, S and Z, numbers and uppercase letters refer to gene exons. For EGF receptor and LDL receptor, respectively, numbers and uppercase letters indicate a particular growth factor domain. For example, PC-4h is the human protein C fourth exon growth factor domain; LDLrBrb is growth factor domain B of rabbit low density lipoprotein receptor. Gaps (-) have been inserted to maximize the homologies among the proteins. Amino acids are designated with the standard single letter code.

FIG. 16 shows the oligonucleotides used to construct growth factor domain replacements.

BEST MODE FOR CARRYING OUT THE INVENTION

Figure 2:
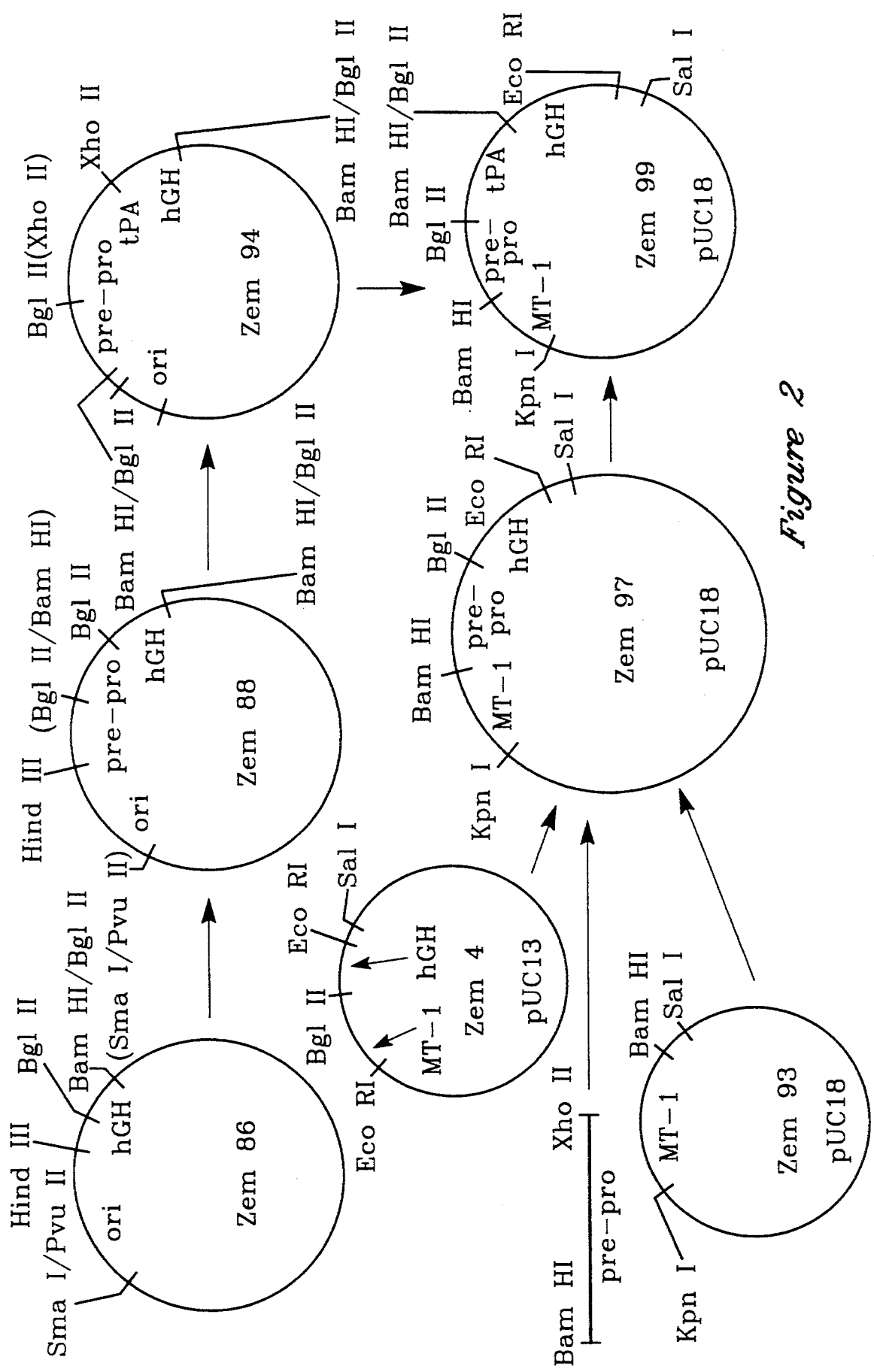
FIG. 2 illustrates the construction of the vector Zem99.

Prior to setting forth the invention, it may be helpful to an understanding thereof to set forth definitions of certain terms to be used herein.

Domain: A three-dimensional, self-assembling array of amino acids of a protein molecule, which contains structural elements necessary for a specific biological activity of that protein.

DNA construct: A DNA molecule, or a clone of such a molecule, either single- or double-stranded, which has been modified through human intervention to contain segments of DNA combined and juxtaposed in a manner which would not otherwise exist in nature.

Plasminogen Activator: A protein which, in the presence of fibrin, can convert the pro-enzyme plasminogen into plasmin.

Native t-PA: A protein having the structure and biological activity of tissue plasminogen activator as isolated from human melanoma cells (see, for example, EP 0041766 A2). Native t-PA has the amino acid sequence of the melanoma cell t-PA, or may contain slight variations in sequence. Such variations, arising from, for example, genetic polymorphisms, will not substantially alter the structure or activity of the protein. The biological activity of native t-PA is characterized by the conversion of the pro-enzyme or zymogen plasminogen into plasmin, which in turn degrades fibrin matrices. Fibrin acts as a cofactor in this activation. Native t-PA may be isolated from cells which naturally produce it, or may be prepared from recombinant cells which have been transfected or transformed with a DNA sequence encoding native t-PA. The amino acid sequence of a representative native t-PA and the DNA sequence encoding it are shown in FIG. 1.

Plasma half-life: The period of time required for the elimination or inactivation of 50% of a substance from the bloodstream of an animal. For t-PA, plasma half life is measured by monitoring the disappearance of t-PA from the bloodstream of a test animal, such as a rat, using, for instance, an enzyme-linked immunosorbent assay (ELISA).

As noted above, native human t-PA is a 72,000 dalton protein which may exist in a two-chain form. The protein contains a number of structural domains which individually and collectively contribute to the biological activity of the protein. One of these domains is called the "growth factor domain" (hereinafter "GF domain") due to its homology with epidermal growth factor (EGF).

To have both fibrin binding activity and serine protease activity, the plasminogen activators of the present invention will contain at least a GF domain, a kringle domain and a serine protease domain. Preferably, the kringle domain will be the $K_2$ domain of native t-PA. Additional kringle domains may also be included as discussed in more detail below. It is also advantageous to include a finger domain in order to provide greater affinity for fibrin. A preferred finger domain is that of native t-PA.

Studies by the inventors have indicated that the GF domain of native t-PA contributes to both its ability to bind fibrin and the regulation of its plasma half-life. By altering the conformation of this domain, the plasma half-life of the protein may be prolonged. This prolongation of half-life may result from an alteration of that region of the molecule which binds to a putative receptor which may be involved in the clearance of t-PA from the bloodstream.

According to the present invention, modifications of the GF domain sequence include the substitution of a plurality of substantially consecutive amino acids of the GF domain of native t-PA. Amino acid substitutions are made in this region with the goal of disrupting the region involved in the rapid clearance of t-PA from plasma without drastically altering the potential receptor region located within the growth factor domain. The loop structure bounded by amino acids 62 and 73 is a primary candidate for the receptor binding region due to its low homology with corresponding regions in other growth factor domain-containing proteins and characteristics which suggest that it is located on the protein surface. It is preferred that substitute amino acids be selected from those found in corresponding positions in growth factor domains of other proteins. Targeted changes may eliminate specific receptor interactions without destroying those features which allow the domain to assume its overall EGF-like conformation, including disulfide bonding between cysteine pairs 51 and 62, 56 and 73, and 75 and 84. In general, it is desirable to maintain the ability of this region to act as a growth factor domain. Toward this end, amino acid substitutions are chosen so as to avoid major changes in conformation but with the goal of changing the chemical nature of one or more amino acid residues at specific positions. For example, it may be desirable to retain certain highly conserved features of growth factor domains. As shown in FIG. 15, these features may include (a) the presence of the sequence Asn-Gly-Gly (NGG) proximate to the second cysteine residue of the t-PA growth factor domain; and (b) the presence of the sequence Cys-X-Cys, where X is any amino acid, corresponding to cysteine residues four and five of the native t-PA growth factor domain.

Preferred substitutions include the substitution of a plurality of substantially consecutive amino acids from the growth factor domain(s) of one or more proteins with a relatively long plasma half-life, such as coagulation factors VII and IX. In addition, more than one region of the growth factor domain of native t-PA may be replaced by the respective blocks of amino acids discussed above. Further, one can substitute a complete growth factor domain from another protein. Other substitutions are made by designing consensus growth factor sequences based on sequences in factor VII, factor IX, protein C, epidermal growth factor and other proteins containing a growth factor domain. Growth factor domains are also found in urokinase, factor X, protein S, protein Z, low density lipoprotein receptor, transforming growth factor, epidermal growth factor receptor, thrombomodulin and thrombospondin. A particularly preferred such consensus sequence is the amino acid sequence methionine-glutamic acid-glycine-asparagine-histidine-leucine-alanine-asparagine (MEGNHLAN), which was substituted for amino acids 63–70 of native t-PA. In certain preferred embodiments, the cysteine residue corresponding to amino acid residue 83 of the native t-PA GF domain is also replaced with another amino acid in order to increase the stability of the resultant molecule. In principle, any amino acid may be substituted for cysteine, although serine and alanine are preferred. A particularly preferred substitute amino acid is serine.

Amino acid substitutions are preferably made by synthesizing oligonucleotides of convenient length, preferably about 30 to 50 nucleotides in length, and assembling them to construct the desired coding sequence. Oligonucleotides of this length permit the design of modular sequences which can then be arranged in a variety of combinations in order to obtain a large number of overall sequences. Such combination is facilitated by designing the oligonucleotides so that when paired, the resulting fragment ends are blunt or complementary to those of oligonucleotide pairs encoding adjacent sequences. It will be understood, however, that complete GF substitutions can be constructed using full-length oligonucleotides. Oligonucleotides provide the added advantage of permitting codon use optimization appropriate to the chosen host cell type.

Alternatively, DNA sequences encoding the GF substitutions may be obtained from cDNA or genomic clones encoding proteins having GF domains. Clones of factor IX (Kurachi and Davie, *Proc. Natl. Acad. Sci. USA* 79:6461–6464, 1982; Anson et al., *Nature* 315:683–685, 1985), factor VII (Hagen et al., *Proc. Natl. Acad. Sci. USA* 83:2412–2416, 1986), protein C (Foster et al., *Proc. Natl. Acad. Sci. USA* 82:4673–4677, 1985), and epidermal growth factor (Gray et al., *Nature* 303:722–725, 1983) have been described. Suitable clones encoding these and other proteins may be obtained by procedures familiar to those having ordinary skill in the genetic engineering art.

The sequences encoding the GF domain substitutions are then inserted into the t-PA sequence at convenient restriction sites. In some cases it will be necessary to use in vitro mutagenesis to properly join the sequences.

In addition to the growth factor domain sequence substitutions discussed above, the proteins of the present invention may contain additional changes in the amino acid sequence of native t-PA. These additional changes or mutations are combined with the GF domain modifications so as to further enhance the desired properties of the molecule, including an increase in fibrin affinity and further increases in plasma half-life. Suitable mutations include amino acid substitutions, deletions or additions. Many such mutations have been previously described, as discussed above, and additional modifications are disclosed herein. Particularly preferred mutations include replacement of the native t-PA K1 domain, amino acid substitutions near the cleavage (activation) site and the removal of the carbohydrate attachment site in the K1 domain. Such mutations are directed toward enhancing the clinical suitability of the resultant t-PA analogs. For example, the K1 domain of native t-PA may be replaced with a kringle domain derived from another protein to enhance the fibrin specificity of the resulting analog. Suitable kringle domains in this regard include the K1, K2, K3, K4 and K5 domains of plasminogen, the K2 domain of native t-PA, the K1 and K2 domains of prothrombin, and the kringle domain of factor XII. The K1 domain of plasminogen is particularly preferred. Modifications to the activation site may increase clot specificity of the t-PA analog by reducing its sensitivity to proteolytic cleavage by plasmin and/or allowing cleavage by thrombin. Modifications of carbohydrate attachment sites increase the uniformity of the protein product and increase plasma half-life. Changes at carbohydrate attachment sites are introduced via oligonucleotide-directed site-specific mutagenesis. By altering the Asn residues at the N-linked glycosylation sites (sequence Asn-X-Ser/Thr, wherein X is any amino acid) to another amino acid residue, glycosylation may be blocked. It is particularly preferred that the Asn residues be changed to Gln residues. Asn may also be changed to Ser or Thr. Additionally, other alterations in the sequence may be introduced for the purpose of blocking glycosylation of the encoded protein. For example, a proline residue in the second position of the sequence Asn-X-Ser/Thr may prohibit glycosylation (Marshall, *Biochem. Soc. Symp.* 40:17–26, 1974), Other substitutions may also be made at this position. The third amino acid of an N-linked glycosylation site may also be changed, preferably to Ala, Cys, Gly, Asn or Gln. Glycosylation sites may be changed individually or in combination. In one preferred embodiment, carbohydrate addition at Asn-117 is blocked by the substitution of a glutamine residue.

According to the present invention, it is preferred to produce these novel proteins through the use of recombinant DNA technology, using cDNA clones or genomic clones as starting materials. Suitable DNA sequences can also be synthesized according to standard procedures, including automated synthesis, or may be obtained from commercial sources. It is preferred to use cDNA clones because, by employing the full-length cDNA encoding native t-PA as starting material for producing modified t-PA, introns are removed so that all exons of the native t-PA are present and correctly oriented with respect to one another. The cDNA can also be used as a template for deletion, alteration or insertion of sequences via oligonucleotide-directed mutagenesis. This methodology provides a means for selecting the optimum combination of functional domains found in native t-PA or in related proteins, and thus provides fibrinolytic agents with enhanced biological activity with respect to fibrin binding and specificity of serine protease activity.

Amino acid substitutions or deletions may be introduced by site-specific mutagenesis using the cloned t-PA DNA sequence or a portion thereof as a template. Techniques for oligonucleotide-directed in vitro mutagenesis are generally known in the art. A preferred such method is that of Zoller and Smith (DNA 3:479–488, 1984). The mutated sequence is, if necessary, joined to the remainder of the t-PA coding sequence, and the complete coding sequence is then inserted into an expression vector.

DNA sequences encoding modified forms of t-PA may be expressed in various host cells, including mammalian cells, yeast and other fungi, and bacteria. Production of recombinant t-PA in bacteria, yeast and mammalian cells is disclosed by, for example, Goeddel et al. (EP 93,619 A1), Meyhack and Hinnen (EP 143,081 A2), and Gill (EP 174,835 A1). Methods for transfecting mammalian cells and for transforming bacteria and fungi with foreign DNA are well known in the art. Suitable expression vectors will comprise a promoter which is capable of directing the transcription of a cloned DNA sequence in a host cell and a functional transcription termination site.

In some instances, it is preferred that expression vectors further comprise an origin of replication, as well as sequences which regulate and/or enhance expression levels, depending on the host cell selected. Suitable expression vectors may be derived from plasmids, RNA and DNA viruses or cellular DNA sequences, or may contain elements of each.

Preferred prokaryotic hosts for use in carrying out the present invention are strains of the bacteria *Escherichia coli*, although Bacillus and other genera are also useful. Techniques for transforming these hosts, and for expressing foreign DNA sequences cloned in them, are well known in the art (see, for example, Maniatis et al., *Molecular Cloning: A Laboratory Manual*, Cold Spring Harbor Laboratory, 1982). Vectors used for expressing foreign DNA in bacterial hosts will generally contain a selectable marker, such as a gene for antibiotic resistance, and a promoter which functions in the host cell. Appropriate promoters include the trp (Nichols and Yanofsky, *Meth. in Enzymology* 101:155, 1983), lac (Casadaban et al., *J. Bact.* 143:971-980, 1980), TAC (Russell et al., Gene 20:231-243, 982), and phage λ promoter systems. Plasmids useful for transforming bacteria include pBR322 (Bolivar et al., *Gene* 2:95-113, 1977), the pUC plasmids (Messing, *Meth. in Enzymology.* 101:20-77, 1983; and Vieira and Messing, *Gene* 19:259-268, 1982), pCQV2 (Queen, *J. Mol. Appl. Genet.* 2:1-10, 1983), and derivatives thereof.

Eukaryotic microorganisms, such as the yeast *Saccharomyces cerevisiae*, or filamentous fungi including Aspergillus, may also be used as host cells. Particularly preferred species of Aspergillus include *A. nidulans, A. niger, A. oryzae,* and *A. terreus.* Techniques for transforming yeast are described by, for example, Beggs (Nature 275:104-108, 1978). Aspergillus species may be transformed according to known procedures, for example, that of Yelton et al. (*Proc. Natl. Acad. Sci. USA* 81:1740-1747, 1984). Expression vectors for use in yeast include YRp7 (Struhl et al., *Proc. Natl. Acad. Sci. USA* 76:1035-1039, 1979), YEp13 (Broach et al., Gene 8:121-133, 1979), pJDB248 and pJDB219 (Beggs, ibid.), and derivatives thereof. Such vectors will generally comprise a selectable marker, such as the nutritional marker TRP1, which allows selection in a host strain carrying a trp1 mutation. Preferred promoters for use in yeast expression vectors include promoters from yeast glycolytic genes (Hitzeman et al., *J. Biol. Chem.* 255:12073-12080, 1980; Alber and Kawasaki, *J. Mol. Appl. Genet.* 1:419-434, 1982; Kawasaki, U.S. Pat. No. 4,599,311) or alcohol dehydrogenase genes (Young et al., in *Genetic Engineering of Microorganisms for Chemicals,* Hollaender et al., eds., p. 335, Plenum, New York, 1982; and Ammerer, *Meth. in Enzymology* 101:192-201, 1983). To facilitate purification of a modified t-PA protein produced in a yeast transformant and to obtain proper disulphide bond formation, a signal sequence from a yeast gene encoding a secreted protein may be substituted for the t-PA pre-pro sequence. A particularly preferred signal sequence is the pre-pro region of the MFα1 gene (Kurjan and Herskowitz, Cell 30:933-943, 1982; Kurjan et al., U.S. Pat. No. 4,546,082; and Singh, EP 123,544).

Higher eukaryotic cells may also serve as host cells in carrying out the present invention. Cultured mammalian cells, such as the BHK, CHO NS-1, SP2/0 and J558L cell lines, are preferred. These and other cell lines are widely available, for example, from the American Type Culture Collection. A particularly preferred adherent cell Nine is the BHK cell line tk$^-$ts13 (Waechter and Baserga, *Proc. Natl. Acad. Sci. USA* 79:1106-1110, 1982), hereinafter referred to as "tk$^-$BHK cells." Expression vectors for use in mammalian cells will comprise a promoter capable of directing the transcription of a cloned gene introduced into a mammalian cell. Particularly preferred promoters include the SV40 promoter (Subramani et al., Mol. Cell Biol. !:854-864, 1981), the MT-1 promoter (Palmiter et al., Science 222:809-814, 1983), and the mouse kappa gene promoter (Bergman et al., *Proc. Natl. Acad. Sci. USA* 81:7041-7045, 1984). Also contained in the expression vectors is a transcription terminator, located downstream of the insertion site for the DNA sequence to be expressed. A preferred terminator is the human growth hormone (hGH) gene terminator (DeNoto et al., Nuc. Acids Res. 2:3719-3730, 1981). In addition, vectors will preferably contain enhancer sequences appropriate to the particular host cell line.

For expression of mutant t-PAs in cultured mammalian cells, expression vectors containing cloned t-PA sequences are introduced into the cells by appropriate transfection techniques, such as calcium phosphate-mediated transfection (Graham and Van der Eb, Virology 52:456–467, 1973; as modified by Wiglet et al., Proc. Natl. Acad. Sci. USA 77:3567-3570, 1980; or as described by Loyter et al., *Proc. Natl. Acad. Sci. USA* 79:422, 1982) or electroporation (Neumann et al., *EMBO J.* 1:841-845, 1982). A portion of the cells take up the DNA and maintain it inside the cell for several days. A small fraction of these cells integrate the DNA into their genome or maintain the DNA in non-chromosomal nuclear structures. These transfectants can be identified by cotransfection with a gene that confers a selectable phenotype (a selectable marker). Preferred selectable markers include the DHFR gene, which imparts cellular resistance to methotrexate (MTX), an inhibitor of nucleotide synthesis; or the bacterial neomycin resistance gene, which confers resistance to the drug G-418, an inhibitor of protein synthesis. After the host cells have taken up the DNA, drug selection is applied to select for a population of cells that are expressing the selectable marker at levels high enough to confer resistance. Selectable markers may be carried on the same vector as the sequence encoding the t-PA analog, or may be carried on a separate vector.

When using methotrexate selection, coamplification can be used to increase expression levels by adding high concentrations of MTX to the culture medium at the time of the initial selection, or by sequentially increasing the drug concentration in the medium, followed by repeated cloning by dilution of the drug-resistant cell lines. Variations exist in the ability to amplify and relate both to the initial genomic configuration (i.e., extrachromosomal vs. chromosomal) of the cotransfected DNA sequences and to the mechanism of amplification itself, in which variable amounts of DNA rearrangements can occur. This is noticed upon further amplification of clones which have been previously shown to be stable. For this reason, it is necessary to clone by dilution after every amplification step. Cells which express the selectable marker are then selected and screened for production of t-PA. Screening may be done, for example, by enzyme-linked immunosorbent assay (ELISA) or by biological activity assays.

The plasminogen activators of the present invention are preferably purified by affinity chromatography using polyclonal or monoclonal antibodies coupled to a suitable matrix, such as CNBr-activated Sepharose. Conventional chemical purification procedures, such as gel filtration, HPLC, etc., may also be employed.

The plasminogen activators of the present invention may be used within pharmaceutical compositions for the treatment of thrombosis. The pharmaceutical compositions will comprise a plasminogen activator in combination with a carrier or diluent, such as sterile water or sterile saline, and may also comprise appropriate excipients and/or solvents. The resulting aqueous solutions may be packaged for use or filtered under aseptic conditions and lyophilized, the lyophilized preparation being combined with a sterile aqueous solution prior to administration.

Typically, an aqueous solution containing 3 g of mannitol and $10^6$ units of the plasminogen activator is prepared under sterile conditions. One ml aliquots of this solution are pipetted into small vials, which are then lyophilized and sealed. For injection, the lyophilized material is combined with 2 ml of sterile water, the water being provided in a sealed ampoule. Administration is preferably by injection. The proteins of the present invention will typically be administered at doses of from about 6 mg to about 100 mg per patient, depending on the weight of the patient and the nature of the thrombus to be dissolved. However, the present invention is not restricted to the above range and the dose may be varied depending on the condition. Determination of proper dose will be apparent to the skilled practitioner.

The following examples are offered by way of illustration, and not by way of limitation.

EXAMPLES

Example 1

Construction of a Full-Length t-PA Clone

The sequence of a native human t-PA cDNA clone has been reported (Pennica et al., Nature 301:214–221, 1983). The sequence encodes a pre-pro peptide of 32–35 amino acids followed by a 527–530 amino acid mature protein.

A cDNA clone comprising the coding sequence for mature t-PA was constructed using as starting material mRNA from the Bowes melanoma cell line (Rijken and Collen, J. Biol. Chem. 256:7035–7041, 1981). This cDNA was then used to construct the plasmid pDR1296. Escherichia coli strain JM83 transformed with pDR1296 has been deposited with the American Type Culture Collection under Accession No. 53347.

Because the pre-pro sequence was not present in the cDNA clone pDR1296, it was constructed from synthesized oligonucleotides and subsequently joined to the cDNA. In the synthesized t-PA pre-pro sequence, cleavage sites for Bam HI and Nco I were introduced immediately 5' to the first codon (ATG) of the pre-pro sequence, and a Bgl II (Sau 3A, Xho II) site was maintained at the 3' end of the pre-pro sequence. The naturally-occurring pre-pro sequence lacks a convenient restriction site near the middle; however, the sequence GGAGCA (coding for amino acids −20 and −19, Gly-Ala) can be altered to GGCGCC to provide a Nat I site without changing the amino acid sequence.

To construct the pre-pro sequence, the following oligonucleotides were synthesized using an Applied Biosystems Model 380-A DNA synthesizer:

ZC131: 5'GGA TCC ATG GAT GCA ATG AAG AGA GGG CTC TGC TGT GTG3'
ZC132: 5'TGG CGC CAC ACA GCA GCA GCA CAC AGC AGAG3'
ZC133: 5'GGC GCC GTC TTC GTT TCG CCC AGC CAG GAA ATC CATG3'
ZC134: 5'AGA TCT GGC TCC TCT TCT GAA TCG GGC ATG GAT TTC CT3'

Following purification, oligomers ZC131 and ZC132 were annealed to produce an overlap of 12 base pairs (Section 1). Oligomers ZC133 and ZC134 were similarly annealed (Section 2). The oligomers were mixed in Pol I buffer (Bethesda Research Labs), heated to 65° C. for five minutes, and slowly cooled to room temperature for four hours to anneal. Ten units of DNA polymerase I were added and the reaction proceeded for two hours at room temperature. The mixtures were electrophoresed on an 8% polyacrylamide-urea sequencing gel at 1,000 volts for 2½ hours in order to size fractionate the reaction products. The correct size fragments (those ..in which the polymerase reaction went to completion) were cut from the gel and extracted.

After annealing, Section 1 was cut with Bam HI and Nat I and cloned into Bam HI+Nat I−cut pUC8 (Vieira and Messing, Gene 19:259–268, 1982; and Messing, Meth. in Enzymology 101:20–77, 1983). Section 2 was reannealed and cut with Nat I and Bgl II and cloned into Bam HI+Nat I−cut pUC8. Colonies were screened with the appropriate labeled oligonucleotides. Plasmids identified as positive by colony hybridization were sequenced to verify that the correct sequence had been cloned.

Section 1 was then purified from a Bam HI+Nat I double digest of the appropriate pUC clone. Section 2 was purified from a Nat I+Xho II digest. The two fragments were joined at the Nat I site and cloned into Bam HI - cut pUC8.

The t-PA sequence of pDR1296 was then joined to the synthesized pre-pro sequence in the following manner (FIG. 2). Plasmid pIC19R (Marsh et al., Gene 32:481–486, 1984) was digested with Sma I and Hind III. The ori region of SV40 from map position 270 (Pvu II) to position 5171 (Hind III) was then ligated to the linearized pIC19R to produce plasmid Zem67. This plasmid was then cleaved with Bgl II, and the terminator region from the human growth hormone gene (De Noto et al., *Nuc. Acids Res.* 9:3719–3730, 1981) was inserted as a Bgl II-Bam HI fragment to produce plasmid Zem86. The synthesized t-PA pre-pro sequence was removed from the pUC8 vector by digestion with Bam HI and Xho II. This fragment was inserted into Bgl II-digested Zem86 to produce plasmid Zem88. Plasmid pDR1296 was digested with Bgl II and Bam HI and the t-PA cDNA fragment was isolated and inserted into Bgl II - cut Zem88. The resultant plasmid was designated Zem94.

The vector Zem99, comprising the MT-1 promoter, complete t-PA coding sequence, and the hGH terminator, was then assembled in the following manner (FIG. 2). A Kpn I-Bam HI fragment comprising the MT-1 promoter was isolated from MThGH111 (Palmiter et. al., *Science* 222:809–814, 1983) and inserted into pUC18 to construct Zem93. Plasmid MThGH112 (Palmiter et al., ibid.) was digested with Bgl II and re-ligated to eliminate the hGH coding sequence. The MT-1 promoter and hGH terminator were then isolated as an Eco RI fragment and inserted into pUC13 to construct Zem4. Zem93 was then linearized by digestion with Bam HI and Sal I. Zem4 was digested with Bgl II and Sal I, and the hGH terminator was purified. The t-PA pre-pro sequence was removed from the pUC8 vector as a Bam HI-Xho II fragment. The three DNA fragments were then joined, and a plasmid having the structure of Zem97 (FIG. 2) was selected. Zem97 was cut with Bgl II and the Xho II t-PA fragment from Zem94 was inserted. The resultant vector is Zem99.

Example 2

Construction of Zem219c

Figure 3:
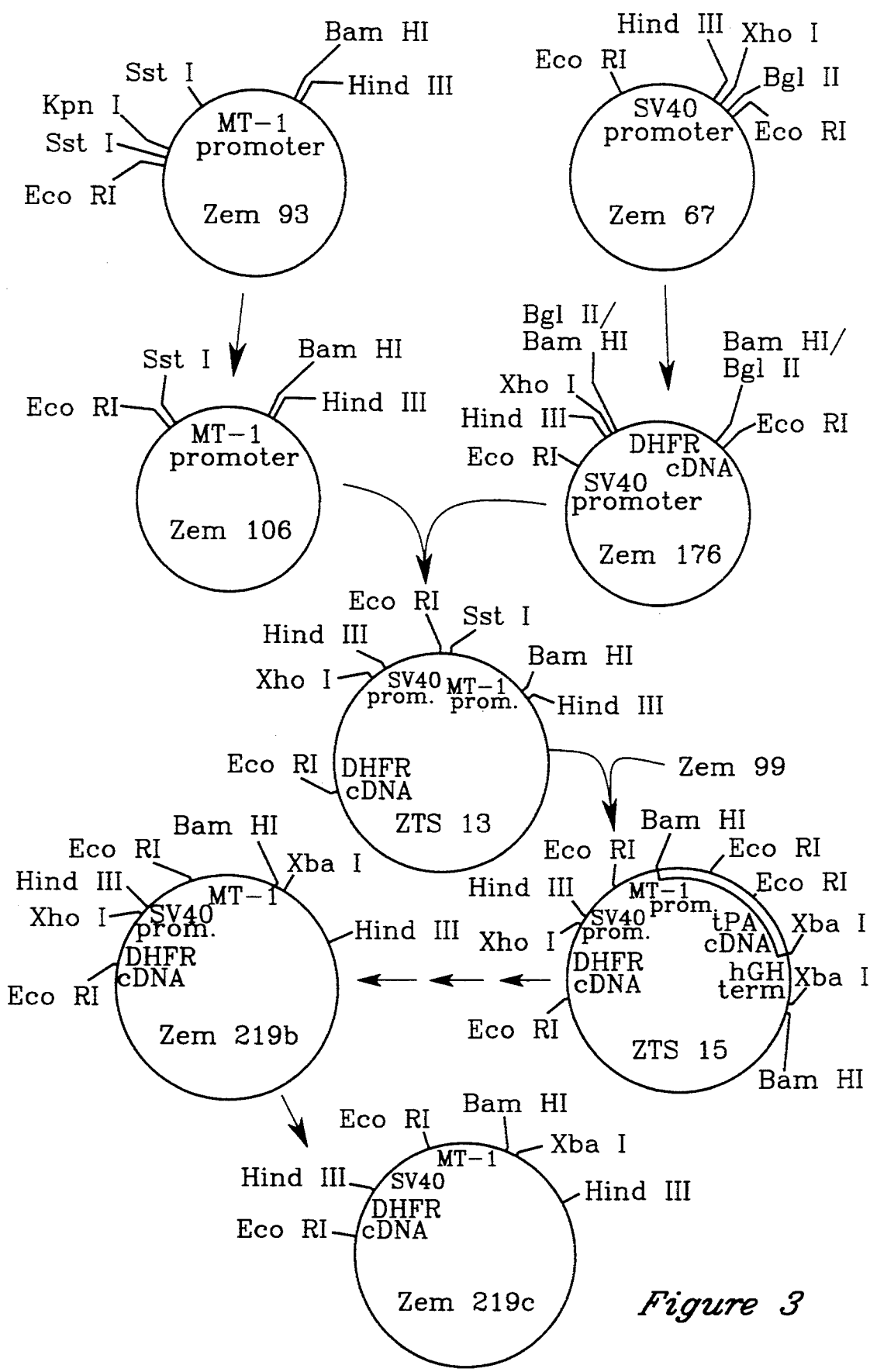
FIG. 3 illustrates the construction of the vector Zem219c.

The vector Zem219c was constructed as shown in FIG. 3. Plasmid pSV2-DHFR (Subramani et al., ibid.) was digested with Cfo I, and the fragment containing the DHFR cDNA and the 3' attached SV40 sequences was isolated, repaired, and ligated to Bam HI linkers. After digestion with Bam HI, an approximately 800 bp fragment containing the entire cDNA and the SV40 terminator region was purified and ligated to Bam HI-digested pUC8. Zem67 (Example 1) was digested with Bgl II and ligated with the Bam HI DHFR-SV40 fragment to generate plasmid Zem176. Plasmid Zem93 was digested with Sst I and re-ligated to generate plasmid Zem106, in which approximately 600 bp of sequence 5' to the MT-1 promoter were eliminated. Plasmid Zem106 was digested with Eco RI and ligated to the Eco RI fragment containing the DHFR gene from plasmid Zem176. The resulting plasmid was designated Zts13. Plasmid Zts13 was digested with Bam HI and ligated to the Bam HI fragment from plasmid Zem99 containing the entire t-PA coding region and hGH terminator sequence. The resulting plasmid was designated Zts15. Zts15 was partially digested with Bam HI, repaired and re-ligated to generate plasmid Zem219, in which the 3' Bam HI site was destroyed. Plasmid Zem219 was partially digested with Xba I, repaired and re-ligated to generate plasmid Zem219a, in which the 3' Xba I site was destroyed. Plasmid Zem219a was digested with Bam HI and Xba I, the vector sequences purified away from the t-PA cDNA sequences, and ligated with an oligomeric Bam HI-Xba I adaptor to generate the vector Zem219b. The Xho I site within the polylinker region of the SV40-DHFR sequence of Zem219b was destroyed by digestion with Xho I, repair and religation of the newly blunted ends. The resulting plasmid was designated Zem219c.

Example 3

Mutagenesis of the t-PA Growth Factor Domain

In order to replace the authentic t-PA GF domain with alternative growth factor sequences, the native t-PA sequence was first modified to place a Kpn I site between the finger and growth factor domain coding sequences. Plasmid Zem99 was digested with Bam HI and Eco RI and the 5' t-PA fragment was recovered and inserted into Bam HI+ Eco RI cut M13mp18. Phage DNA was prepared and 100 μl of the DNA solution was used to infect *E. coli* RZ1032 in 100 μl of YT medium supplemented with 0.1 μg/ml uridine. This culture was incubated at 37° C., with vigorous shaking, overnight. Growing the M13 in RZ1032 produces phage containing uridine which are viable in RZ1032 but not in JM101.

The cells were spun out, and the phage supernatant was used to reinfect *E. coli* RZ1032. This second passage was performed to dilute out any JM101-derived phage which contained no uracil. Again, the cells were spun out and the phage were plated on JM101 and RZ1032. Normal viability was observed on RZ1032 plates (indicating phage at $10^9$ pfu/ml), but no plaques were observed on JM101 cells. A complementary strand primed with the mutagenic oligonucleotide was then produced in vitro. The new strand, containing the mutation, contained thymidine and was therefore viable in JM101; the wild-type template was not.

Template DNA was prepared by PEG precipitation of the phage supernatant followed by phenol-chloroform extraction and ethanol precipitation. One μg of this template DNA was hybridized with 10 μg of oligonucleotide ZC986 by briefly boiling, incubating at 65° C. for 5 minutes, and then slowly bringing the temperature down to 4° C. before adding 10 μl 0.2M HEPES pH 7.8, 2 μl 100 mM DTT, 1 μl 1M MgCl$_2$, 20 μl 12.5 mM each dNTP, 10 μl 10 mM ATP, 1 μl 2.5 U/μl Klenow, and 2 μl 1 U/μl T$_4$ DNA ligase, final volume adjusted to 100 μl with H$_2$O. After extension at 37° C. for 2 hours, the DNA was transfected into competent *E. coli* JM101 cells. A control extension (minus oligonucleotide) was performed to compare the amount of background produced by extension by priming on contaminating RNA or DNA species. The transfection produced zero plaques with unmutagenized template, 150 on control extension (minus oligonucleotide) and 300 with mutagenized template.

The plates were screened by hybridizing a plaque lift with $^{32}$P-labeled mutagenic oligonucleotide and washing in 3M TMACl (Wood et al., *Proc. Natl. Acad. Sci. USA* 82:1585–1588, 1985) at Tm-5° C. for 30 minutes and also by sequencing randomly picked plaques. One positive clone was obtained.

Figure 4:
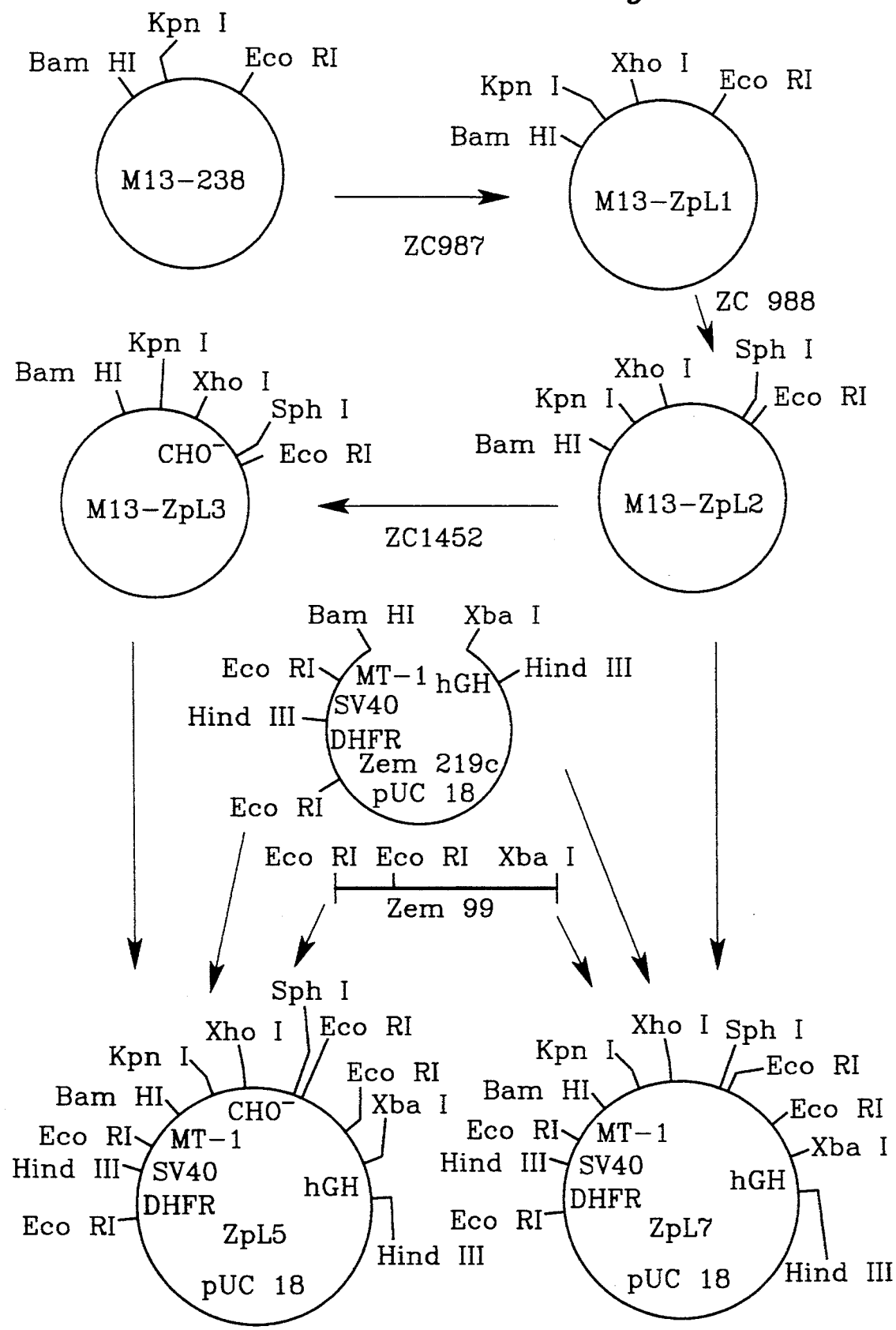
FIG. 4 illustrates the construction of the vector ZpL7.

The mutagenized Bam HI-Eco RI fragment containing the Kpn I site was further mutagenized to insert an Xho I site at the 3' end of the GF domain. Template DNA was prepared from the M13 phage clone containing the Kpn I site by PEG precipitation of the phage supernatant followed by phenol-chloroform extraction and ethanol precipitation. One μg of this DNA was hybridized with 10 μg of oligonucleotide ZC987 (5' CAC GTG GCT CGA GTA TCT ATT TC 3'). The mixture was boiled briefly, incubated at 65° C. for 5 minutes, and the temperature brought slowly down to 4° C. before adding 10 μl of 0.2M ttEPES pH 7.8, 2 μl of 100 mM DTT, 1 μl of 1M MgCl₂, 20 μl of 2.5 mM each dNTP, 10 μl of 10 mM ATP, 2.5 units of DNA polymerase I (Klenow fragment) and 2 units of T₄ DNA ligase, final volume adjusted to 100 μl with H₂O. After extension at 37° C. for 2 hours, the DNA was transfected into competent *E. coli* JM101 cells. The plates were screened by hybridizatior, and after sequence confirmation of the mutagenesis, the new phage clone (ZpL1) was used to prepare template for a second mutagenesis. Oligonucleotide ZC988 (5' CTC AGA GCA TGC AGG GG 3') was used to introduce an Sph I site at the 3' end of the first kringle domain. The mutagenesis was confirmed and the phage clone was designated ZpL2. Replicative form DNA was prepared from ZpL2 and the Bam HI-Eco. RI fragment comprising the 5' portion of the t-PA coding sequence was isolated. This fragment was ligated to the partial Eco RI-Xba I 3' t-PA fragment from Zem99 and Bam HI+Xba I digested Zem219c (FIG. 4). The resulting construct was designated ZpL7.

Figure 5:
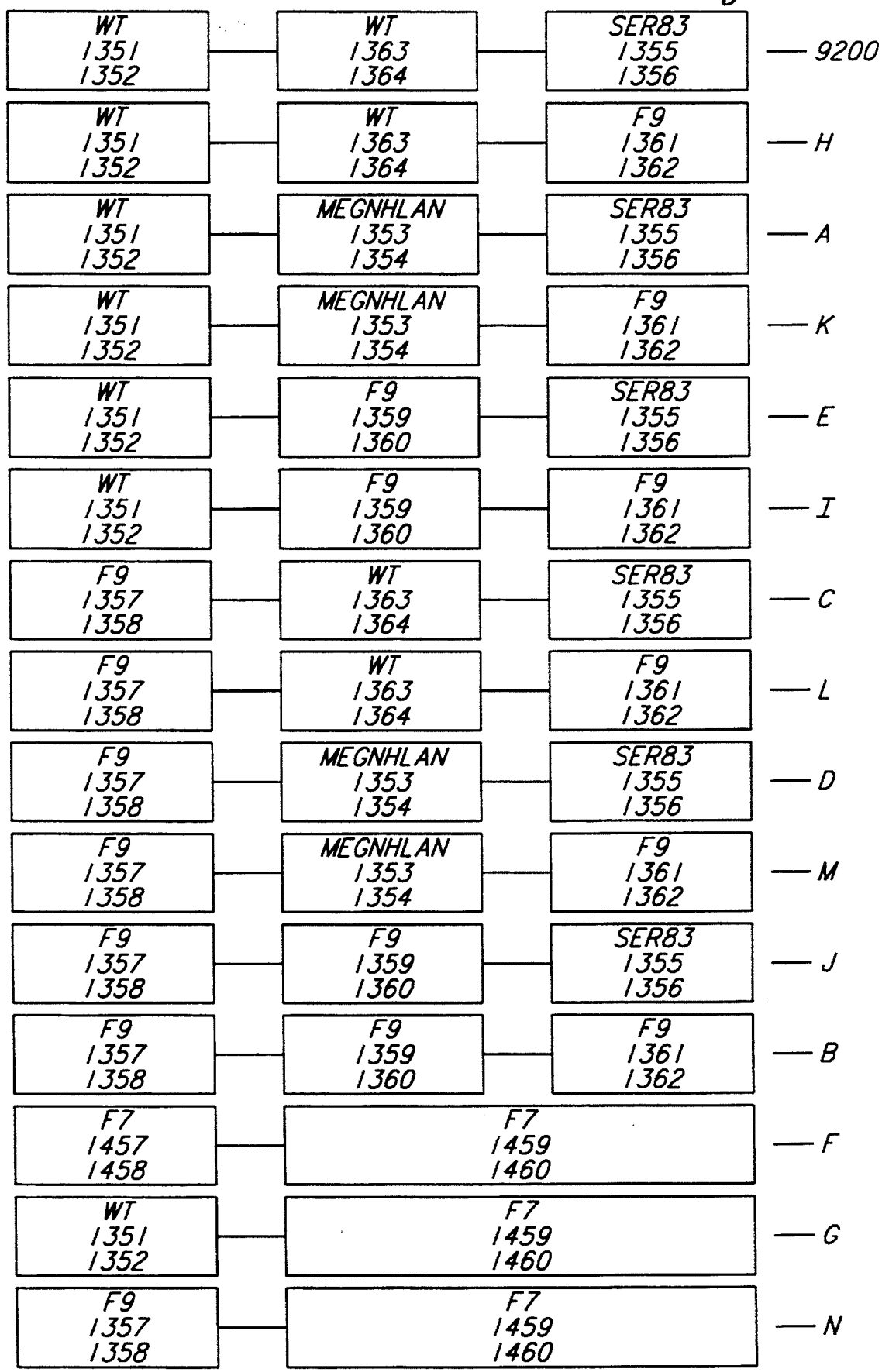
FIG. 5 illustrates certain growth factor domain sequence substitutions, together with the combinations of oligonucleotides encoding the chimetic domains.

Growth factor domain replacements were constructed using the oligonucleotides shown in Table 1. The eighteen oligonucleotides are combined in various combinations of four or six sequences to generate the combinations shown in FIG. 5. 500 ng of each oligonucleotide was incubated in a separate tube containing 50 mM Tris-HCl (ph 8.0), 10 mM MgCl₂, 150 mM dithiothreitol containing 10 μCi (0.3 μM) ³²P-ATP and 0.5 units T₄ polynucleotide kinase at 37° C. for 30 minutes (total reaction volume=30 μl). Five μl aliquots of reaction mixtures containing specific oligonucleotides were mixed in the combinations specified in FIG. 5 (total volume of 20 μl when four oligonucleotides were mixed; 30 μl when six were mixed). One unit of T₄ DNA ligase was added and the mixtures were incubated at room temperature for two hours. The ligated oligonucleotide assemblies were electrophoresed on a 5% polyacrylamide gel containing 8M urea. The bands corresponding to the full length assembled fragments were excised, eluted overnight in 0.3M sodium acetate and the DNA was ethanol precipitated. The oligonucleotide assemblies were diluted 1-, 10- and 50-fold and added to ligation mixtures with purified Kpn I, Xho I-cut ZpL7. Correctly substituted plasmids were identified initially by Southern blot analysis and then by sequencing across the entire substituted region. Referring to FIG. 5, Fragment A replaces t-PA amino acids 63–70 with the sequence MEGNHLAN, Fragment B replaces t-PA amino acids 51–84 with the entire growth factor domain of human factor IX, Fragment C replaces t-PA amino acids 51–60 with the corresponding region of human factor IX, Fragment D replaces t-PA amino acids 51–60 with the corresponding region of factor IX and amino acids 63–70 with MEGNHLAN, Fragment E replaces t-PA amino acids 63–70 with the corresponding region of human factor IX, Fragment F replaces t-PA amino acids 51–84 with the entire growth factor region of human factor VII and Fragment G replaces t-PA amino acids 63–84 with the corresponding region of human factor VII. In fragments A, C, D and E the free cysteine at 83 is changed to serine to enhance protein stability.

The sequences of representative oligonucleotide combinations and the encoded amino acid sequences are shown in FIG. 6. The paired oligonucleotides (1351+1352, 1353+1354, 1355+1356, 1357+1358, 1359+1360, 1361+1362, 1363+1364, 1457+1458, and 1459+1460) may also be assembled in other combinations as shown in FIG. 5.

TABLE 1

ZC1351 (27)
CTG TTA AAT CTT GTT CTG AAC CTA GAT GTT TTA ATG GAG GA

ZC1352 (27)
ATT AAA ACA TCT AGG TTC AGA ACA AGA TTT AAC AGG TAC

ZC1353 (27)
ACA TGC ATG GAA GGA AAT CAT CTT GCT AAT TTT GTT TGT CAA TGT CCT

ZC1354 (27)
TTG ACA AAC AAA ATT AGC AAG ATG ATT TCC TTC CAT GCA TGT TCC TCC

ZC1355 (27)
GAA GGA TTT GCT GGA AAA TCT TGT GAA AAT GAT AC

ZC1356 (27)
TCG AGT ATC AAT TTC ACA AGA TTT TCC AGC AAA TCC TTC AGG ACA

ZC1357 (27)
CTG TTA AAT CTT GTG AAT CTA ATC CTT GTC TTA ATG GAG GA

ZC1358 (27)
ATT AAG ACA AGG ATT AGA TTC ACA AGA TTT AAC AGG TAC

ZC1359 (27)
TCT TGT AAA GAT GAT ATT AAT TCA TAT GAA TGT TGG TGT CCT

ZC1360 (27)
CCA ACA TTC ATA TGA ATT AAT ATC ATC TTT ACA AGA TCC TCC

ZC1361 (27)
TTT GGA TTT GAA GGA AAA AAT TGT GAA ATT GAT AC

ZC1362 (27)
TCG AGT ATC AAT TTC ACA ATT TTT TCC TTC AAA TCC AAA AGG ACA

TABLE 1-continued ZC1363                                        27
ACA TGT CAA CAA GCT CTT TAT TTT TCT GAT TTT GTT TGT CAA TGT
CCT ZC1364                                        27
TTG ACA AAC AAA ATC AGA AAA ATA AAG AGC TTG TTG ACA TGT TCC
TCC ZC1457
TCG GTA CCT GTT AAA TCT TCT GCT TCT TCT CCT TGT CAA AAT GGA
GGA TCT TGT AAA GAT CAA CTT CAA ZC1458
AGC CAT GGA CAA TTT AGA ACA CGA AGA AGA GGA ACA GTT TTA CCT
CCT AGA ACA TTT CTA GTT GAA GTT ZC1459
TCT TAC ATA TCT TTT TGT CTT CCT GCT TTT GAA GGA AGA AAT TGT
GAA ATT GAT ACT CGA GCT ZC1460
AGA ATG TAT ACA AAA ACA GAA GGA CGA AAA CTT CCT TCT TTA ACA
CTT TAA CTA TGA GCT CGA To construct expression vectors for the modified t-PA sequences, the vector ZpL7 was digested with Kpn I and Xho I and the vector fragment was gel purified. Vector DNA was ligated with each of the growth factor replacement fragments A, B, D, F and G. The ligation mixtures were used to transform competent *E. coli* HB101 cells. Clones were picked and DNA was prepared, digested with Eco RI and fractionated on a 1% agarose gel. The DNA was transferred to nitrocellulose and probed with the appropriate $Y^{32}p$-labeled oligonucleotide to confirm the presence of the substitutions. The resultant plasmids, designated ZpL7A, B, D, F and G, were digested with Eco RI and Bam HI and the 5' t-PA fragments were cloned into M13 phage vectors and sequenced for further confirmation. The plasmids were then transfected into tk⁻BHK cells and high producing clones were scaled up for protein production and characterization.

Example 4

Mutant t-PA with Altered Growth Factor Domain and Reduced Glycosylation

Native t-PA contains a glycosylation site (amino acids 117–119, sequence Asn-Ser-Ser) in the first kringle domain. This site can be mutagenized to prevent carbohydrate attachment. A preferred mutation is the replacement of the Asn residue with Gln.

To replace the Asn in the K1 glycosylation site of the GF replacement mutants described in Example 3, template DNA is prepared from phage ZpL2 and mutagenized with oligonucleotide ZC1452 (5' CAA CGC GCT AGA TTG CCA GTT GGT 3'). The resultant phage clone is designated ZpL3.

Replicative form DNA is prepared from ZpL3 and the Bam HI-Eco RI fragment comprising the 5' portion of the t-PA coding sequence is isolated. This fragment is ligated to the partial Eco RI-Xba I 3' t-PA fragment from Zem99 and Bam HI+Xba I digested Zem219c. The resultant vector is digested with Kpn I and Xho I and the vector fragment is gel purified. Vector DNA is ligated with each of the growth factor replacement fragments described in Example 3. The ligation mixtures are used to transform competent *E. coli* HB101 cells. Clones are picked and the GF domain replacements are confirmed by hybridization and sequence analysis. The plasmids are transfected into tk⁻BHK cells and high producing clones are scaled up for protein production and characterization.

Example 5

Replacement of t-PA Kringle with Plasminogen Kringle

The native t-PA coding sequence was altered to encode the first kringle domain of plasminogen in place of the first kringle (K1) domain of native t-PA. Two forms were constructed: one encoding aspartic acid at amino acid 96, the second encoding asparagine at amino acid 96.

A. Asp (96) Plasminogen Kringle

Plasmid pK1 comprises a coding sequence for the K1 domain of plasminogen, the sequence of which is shown in FIG. 7. It was constructed from a series of eleven oligonucleotides designated PK1-1, PK1-2, PK1-3, —PK1-12, the sequences of which are shown in Table 2.

TABLE 2

| Oligo-nucleotide | Sequence |
|---|---|
| PK1-1 | 5'GAT CCA CGC GTG CCA CGT GCA AGA CCG GTG ATG GTA AAA ACT ACC GAG GTA CCA TGT CCA AGA CC3' |
| PK1-2 | 5'AAA AAC GGT ATT ACA TGT CAG AAA TGG TCA TCT ACT AGT CCA CAC CGG CCG CGG TTT TCT3' |
| PK1-3 | 5'CCA GCT ACC CAT CCA TCT GAA GGC CTG GAA GAG AAT TAC TGT AGG AAT CCA GAT AAC GAT3' |
| PK1-4 | 5'CCT CAG GGT CCC TGG TGT TAC ACC ACA GAC CCC GAG AAG AGG TAC GAC TAC TGC GAT ATC GCA TG3' |
| PK1-5 | 5'CCG TTT TTG GTC TTG G3' |
| PK1-6 | 5'GTA GCT GGA GAA AAC CG3' |
| PK1-7 | 5'CCC TGA GGA TCG TTA TC3' |
| PK1-9 | 5'CGA TAT CGC AGT AGT CGT ACC TCT TCT C3' |
| PK1-10 | 5'GAT CCT CAG GGT CCC TGG TGT TAC ACC ACA3' |
| PK1-11 | 5'GAC CCC GAG AAG AGG TAC GAC TAC TGC GAT ATC GCA TC3' |
| PK1-12 | 5'GGG GTC TGT GGT GTA ACA CCA GGG ACC CTG AG3' |

The coding sequence for nucleotides 1 through 182 of the plasminogen K1 domain was constructed from oligonucleotides PK1-1 through PK1-7 in the following manner. 100 pmole each of the oligonucleotides PK1-1, PK1-2, PK1-3 and PK1-4 were phosphorylated at their 5' termini. The phosphorylated oligonucleotides were mixed with 100 pmole each of PK1-5, PK1-6, and PK1-7. The mixture was precipitated with ethanol, and the precipitate was resuspended in H₂O and heated for 3 minutes at 90° C. The solution was left to stand at room temperature for ten minutes, then placed on ice. To the chilled mixture was added 10 μl of 660 mM Tris HCl, pH 7.6, containing 6.6 mM MgCl₂, 10 μl of 0.1M dithiothreitol, 10 μl of 5 mM ATP, and 1000 units of T₄ DNA ligase. The mixture was incubated 15 hours at 14° C. Ethanol was added and the precipitate was recovered and resuspended in 20 μl of TE buffer (10 mM Tris-HCl, 1 mM EDTA, pH 8.0), followed by the addition of an equal volume of alkali loading buffer (20 mM NaCl, 2 mM EDTA, 80% formamide, 0.1% xylene cyanol and 0.1% bromphenol blue). The mixture was heated for three minutes at 90° C. and electrophoresed on a 6% polyacrylamide gel containing 8.4M urea for one hour at 300 volts. The gel was stained with ethidium bromide and a 250 bp band was recovered by electrophoretic transfer to DEAE-cellulose paper (Dretzen et al., *Anal. Biochem.* 112:295–298, 1981). The recovered DNA was solubilized in 100 μl of TE buffer and the fragment was designated PK1-n. PK1-n was C-tailed at the 3' terminus by combining 10 μl of PK1-n with 2 μl of 100 mM sodium cacodylate—25 mM HEPES, pH 7.6, 6.2 μl of 1 mM dCTP, 10 units terminal deoxynucleotidyl transferase and 5 μl of H₂O. The reaction mix was incubated at 37° C. for 10 minutes, then extracted with phenol:chloroform (1:1).

One μl of 3'-oligo (dG) tailed pUC9 (obtained from Pharmacia) was cleaved with Sma I. The linearized, tailed plasmid was added to the C-tailed PK1-n. The mixture was then ethanol precipitated and the DNA was resuspended in 0.5 μl of 2M KCl and 9.5 μl of TE buffer, and incubated at 65° C. for 10 minutes, then cooled to room temperature. To the cooled mixture were added 5 μl of 0.2M Tris HCl, pH 7.5, containing 0.1M MgCl₂ and 0.1M dithiothreitol, 20 μl of 2.5 mM dNTPs, 10 μl of 5 mM ATP, 53 μl H₂O, 5 units DNA polymerase I (Klenow fragment), and 300 units T₄ DNA ligase (final volume of 100 μl). The mixture was incubated at 14° C. for 12 hours, then used to transfect *E. coli* JM83.

The transfected JM83 cells were probed with PK1-6 using the method of Wallace et al. (*Nuc. Acids Res.* 9:879–894, 1981). Twenty positive clones were sequenced and two were selected: #1-3, including base pairs 1-170, and #8-5, including base pairs 68-186 (see FIG. 9).

Figure 9:
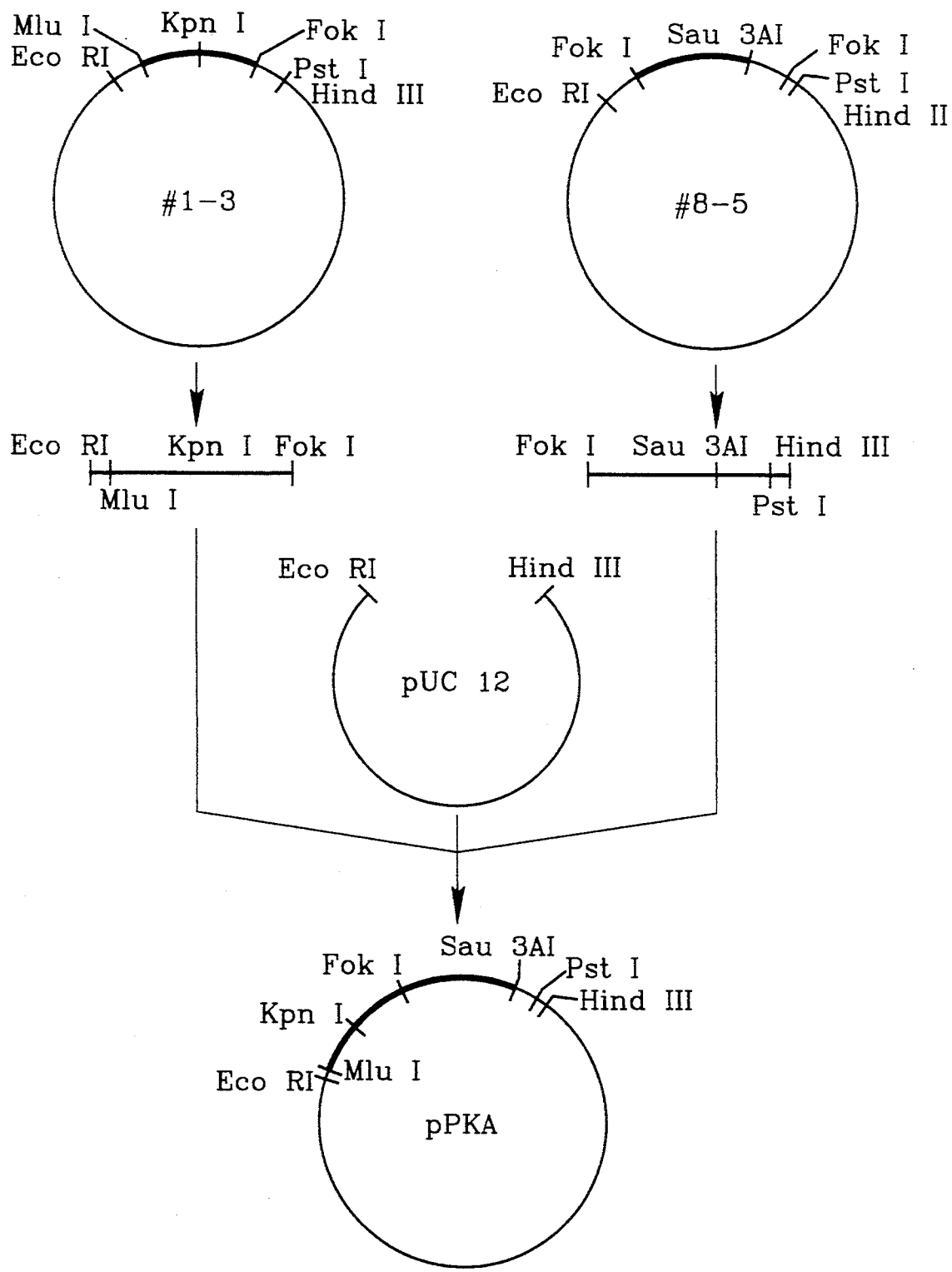
FIG. 9 illustrates the construction of plasmid pPKA.

Referring to FIG. 9, clone #1-3 was digested with Eco RI and Fok I, and a 130 bp fragment containing a Kpn I site was recovered. Similarly, clone #8-5 was digested with Fok I and Hind III, and a 90 bp fragment was recovered. The two fragments were joined to Eco RI, Hind III-digested pUC12 and the resultant plasmid was designated pPKA. This plasmid thus contains a DNA sequence corresponding to nucleotides 1-182 of the plasminogen K1 sequence.

The remainder of the K1 sequence was constructed using oligonucleotides PK1-9, PK1-10, PK1-11 and PK1-12. One pmole each of the oligonucleotides was phosphorylated at the 5' end, and the combined oligos were mixed with 40 μg of Bam HI, Sph I-digested M13tg130RF (obtained from Amersham). To this mixture were added 4 μl of 660 mM Tris-HCl, pH 7.6, containing 66 mM MgCl₂, and 22 μl of H₂O. The solution was heated for three minutes at 90° C. and allowed to cool to room temperature over a period of one hour. Four μl of 0.1M dithiothreitol, 4 μl of 5 mM ATP, and 300 units of T₄ DNA ligase were added, and the mixture was incubated for 12 hours at 14° C. The resulting phage clone, designated M13PKB RF (FIG. 10), contained nucleotides 183 through 250 of the plasminogen K1 sequence.

Figure 10:
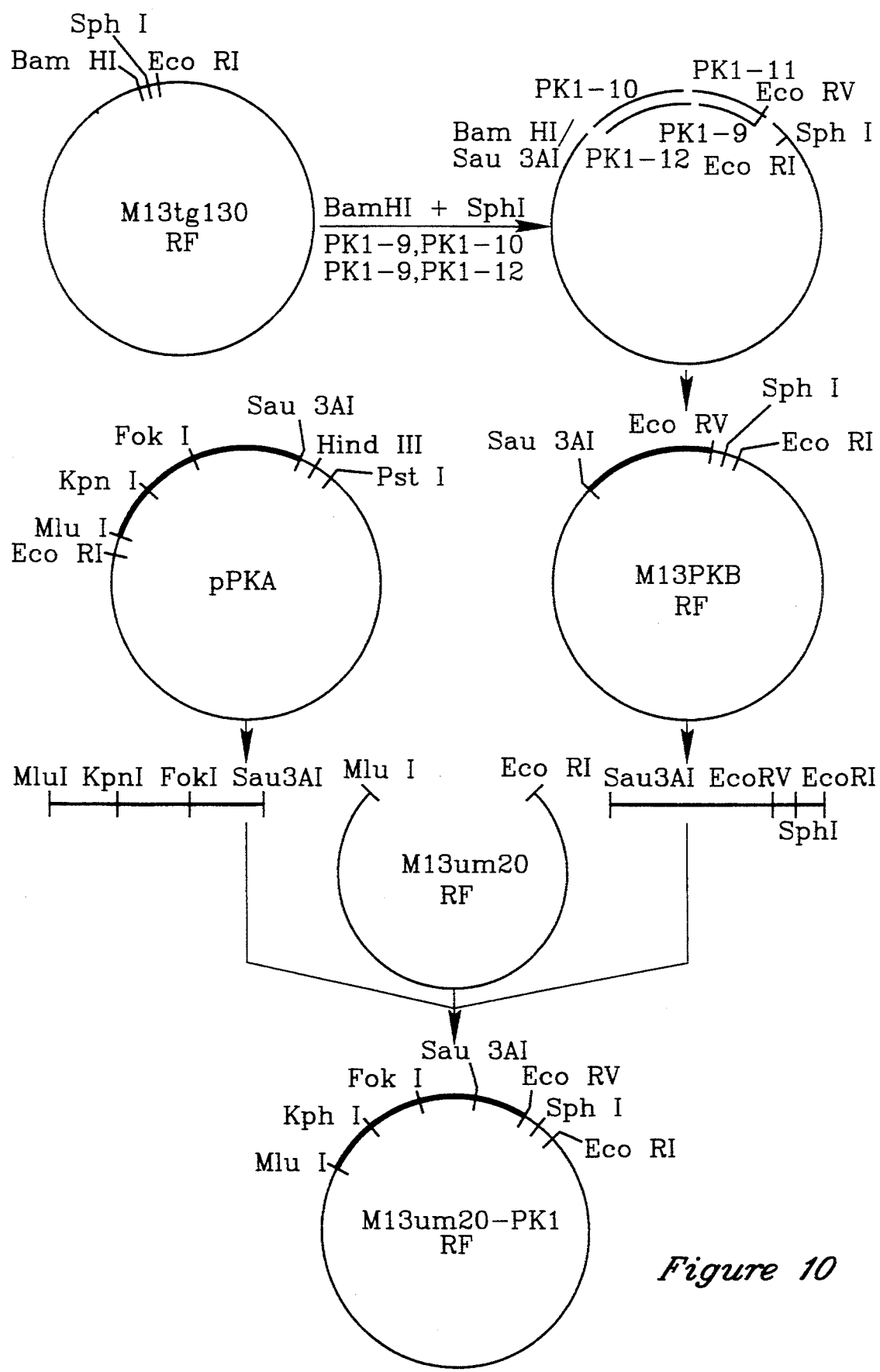
FIG. 10 illustrates the construction of a vector containing the plasminogen K1 coding sequence.

The assembly of the complete plasminogen K1 coding sequence is illustrated in FIG. 10. Plasmid pPKA was digested with Mlu I and Sau 3AI, and a 176 bp fragment was recovered. M13PKB RF was digested with Sau 3AI and Eco RI, and an 88 bp fragment was recovered. These fragments were joined to Mlu I, Eco RI-digested M13um20 RF (obtained from IBI), and the resultant plasmid was designated M13um20-PK1.

Figure 11:
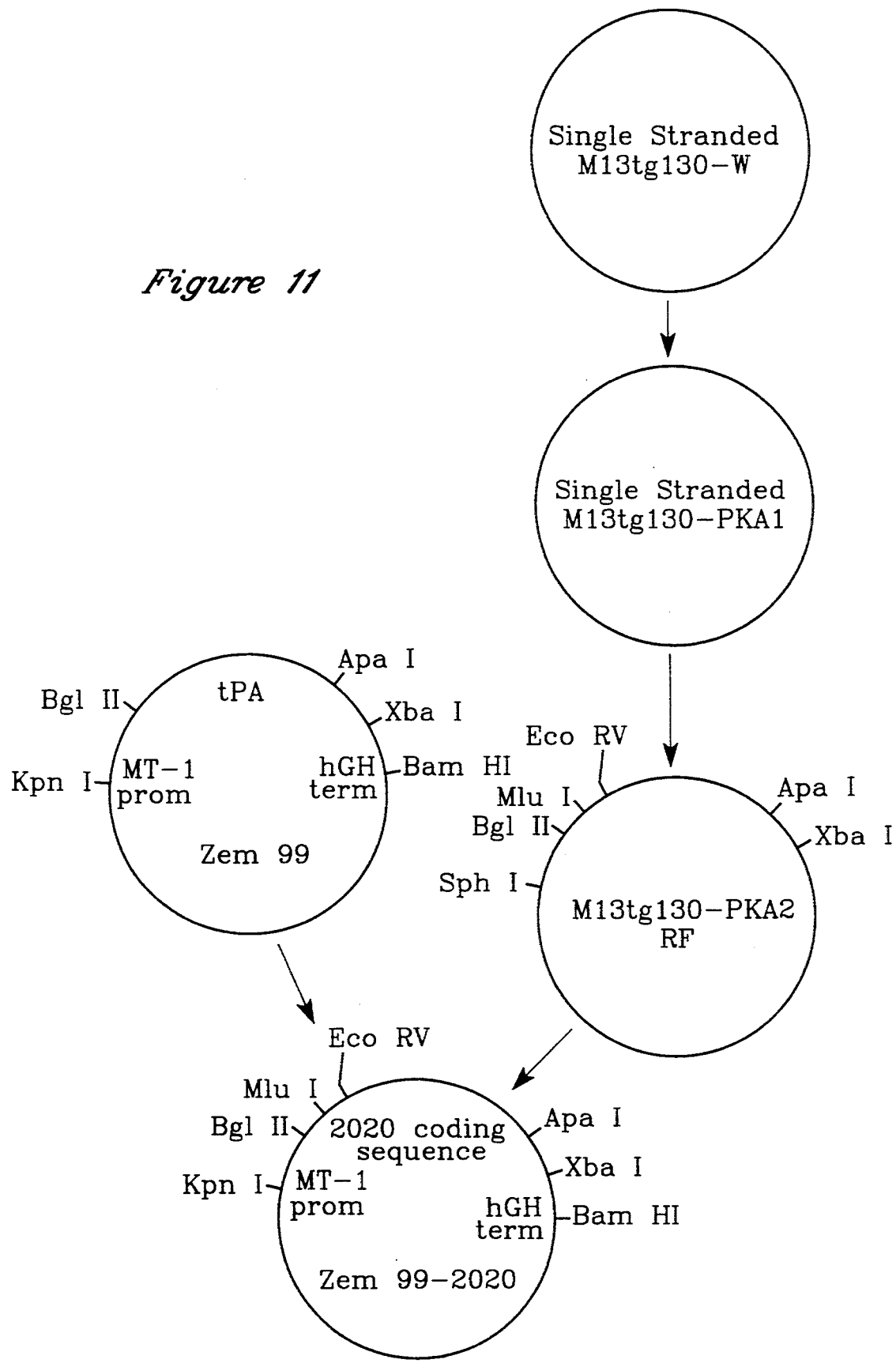
FIG. 11 illustrates the construction of plasmid Zem99-2020.
Figure 12:
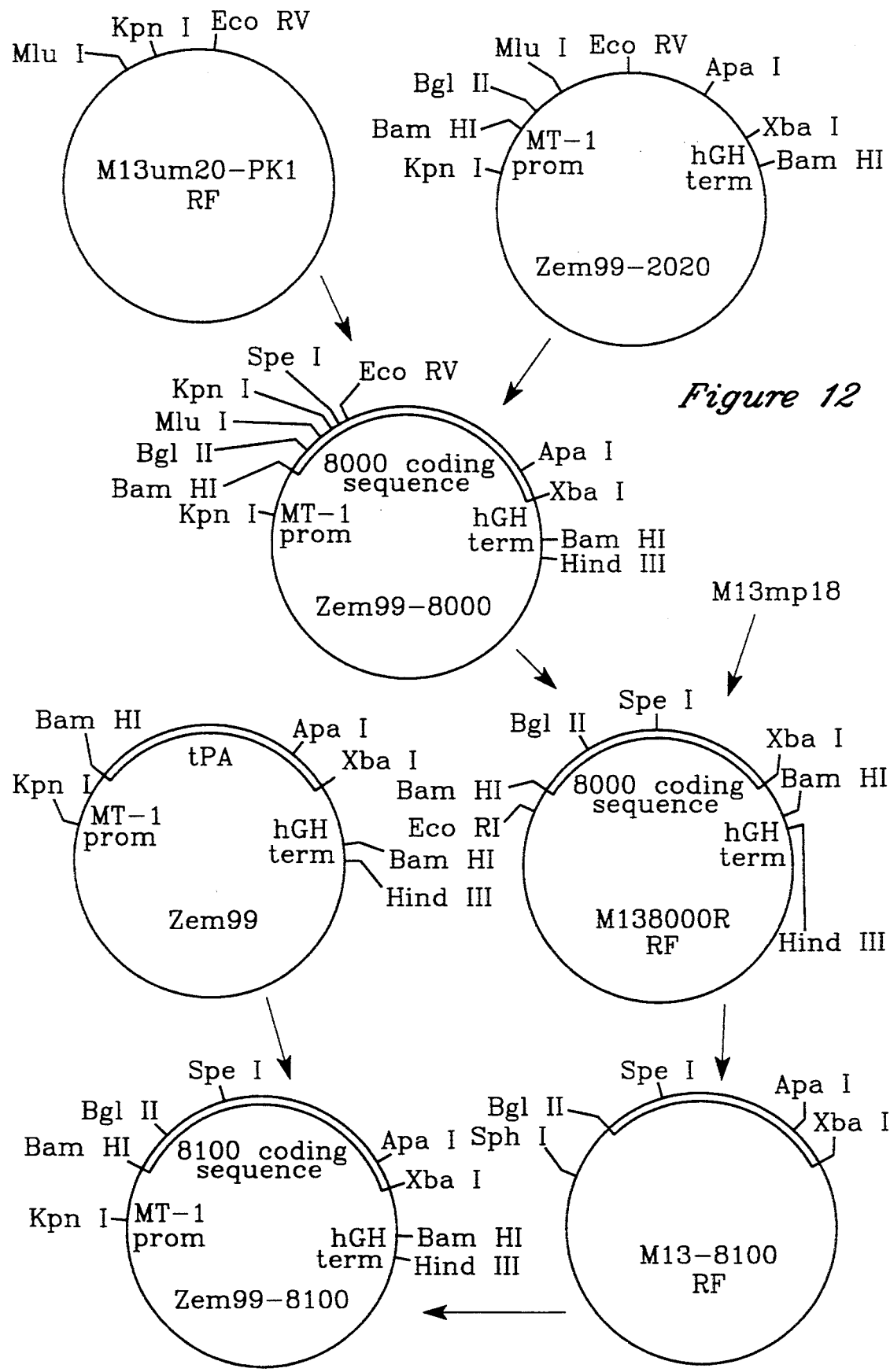
FIG. 12 illustrates the construction of the plasmids Zem99-8000 and Zem99-8100.

The PK1 coding sequence was then inserted into the t-PA cDNA as a replacement for the t-PA Kringle 1 sequence (FIGS. 11 and 12). The t-PA sequence was first mutagenized to insert Mlu I and Eco RV sites. Plasmid pDR1496 was digested with Sph I and Xba I, and the 2.1 kb fragment comprising the alpha factor and t-PA sequences was isolated. (*S. cerevisiae* strain E8-11C transformed with pDR1496 has been deposited with American Type Culture Collection under Accession No. 20728.) This fragment was joined to Sph I, Xba I-digested M13tg130 (RF), and the resultant phage was designated M13tg130-W. Single-stranded phage DNA was then annealed to an oligonucleotide (5' GCA CGT GGC ACG CGT ATC TAT TTC 3') and mutagenesis was carried out according to standard procedures. The mutagenized phage was designated M13tg130-PKA1. Single-stranded DNA of M13tg130-PKA1 was isolated and mutagenized by the one-primer method with an oligonucleotide having the sequence 5' CTC AGA GCA TTC CAG GAT ATC GCA GAA CTC 3'. Single-stranded DNA was prepared from the mutagenized phage and sequenced. A clone containing an Mlu I site at the 5' end and an Eco RV site at the 3' end of the Kringle 1 coding sequence was selected and designated M13tg130-PKA2.

Replicative form DNA was prepared from M13tg130-PKA2 and was digested with Bgl II and Apa I. The fragment containing the Mlu I and Eco RV sites was recovered and joined to Bgl II, Apa I-digested Zem99, as shown in FIG. 11. The resultant plasmid was designated Zem99-2020.

The PK1 sequence was then inserted into the t-PA cDNA. M13um20-PK1 RF was digested with Mlu I and Eco RV, and the 336 bp fragment was recovered. This fragment was joined to Mlu I, Eco RV-digested Zem99-2020 to construct Zem99-8000 (FIG. 12).

B. Asn (96) Plasminogen Kringle

A second plasminogen K1 sequence encoding Asn at position 96 was constructed (FIG. 12). Zem99-8000 was digested with Bam HI, and the fragment containing the Bgl II site was recovered. This fragment was joined to Bam HI cut M13mp18 to construct M13-8000R. An oligonucleotide primer (sequence 5' TTT TTA CCA TTA CCG GTC TT 3') was annealed to single-stranded M13-8000R, and mutagenesis was carried out according to routine procedures for the one-primer method. Clones were screened and sequenced, and double-stranded DNA, designated M13-8000RF, was prepared from a positive clone. This phage was digested with Bgl II and Apa I, and the t-PA fragment was isolated and joined to Bgl II, Apa I - cut Zem99. The resultant plasmid was designated Zem99-8100.

Plasmids Zem99-8000 and Zem99-8100 have been deposited (as *E. coli* RRI transformants) with The Fermentation Research Institute, Agency of Industrial Science and Technology, Ministry of International Trade and Industry, Japan, under Accession Nos. FERM P-9272 and FERM P-9315, respectively.

Plasmid Zem99-8000 was digested with Spe I and Hind III and the fragment containing the 3' mutant t-PA coding sequence and the entire hGH terminator was gel purified. Plasmid ZpL7 was partially digested with Hind III and completely digested with Xho I and the vector sequences were purified away from the 3' t-PA coding sequence and the hGH terminator. Oligonucleotides ZC1639 and ZC1640 (Table 3) were annealed and the resulting Xho I to Spe I fragment (encoding the 5' portion of the plasminogen K1 kringle) was combined in a ligation reaction with the above two purified fragments. The resulting plasmid was designated 8900. To construct chimetic sequences encoding t-PA derivatives comprising the GF and K1 substitutions, plasmid 8900 is digested with Bam HI and Xho I and the GF region is replaced with the Bam HI to Xho I region isolated from one of plasmids ZpL7A-N.

TABLE 3

| ZC 1639: | 5'T CGA GCC ACG TGC AAG ACC GGT GAT GGT AAA AAC TAC CGA GGA ACC ATG TCC AAG ACC AAA AAC GGT ATT ACA TGT CAG AAA TGG TCA TCT A3' |
|---|---|
| ZC 1640: | 5'CT AGT AGA TGA CCA TTT CTG ACA TGT AAT ACC GTT TTT GGT CTT GGA CAT GGT TCC TCG GTA GTT TTT ACC ATC ACC GGT CTT GCA CGT3' |

Example 6

Site-Specific Mutagenesis of the Activation Site

For site-specific mutagenesis, a 472 bp Eco RI fragment comprising the t-PA sequence from bp 802 to bp 1274 was isolated from Zem99 and cloned into the Eco RI site of M13mp18 (replicative form). The recombinant phage were transfected into *E. coli* (JMI01), and anti-sense strand DNA was isolated.

Site-specific mutagenesis was then carried out on the single-stranded anti-sense template DNA using one of the mutagenic primers shown in Table 4 and ZC87 as second primer. Oligonucleotides ZC487, 488, 489 and 620 change the Phe at position 274 to Glu, Gly, Arg or Pro, respectively. Oligonucleotides ZC797, 874, 1013 and 1027 change the Arg at position 275 to Gly, Leu, Pro or Asp, respectively. Oligonucleotide 621 introduces a Leu in place of the Lys at position 277. Oligonucleotide 928 changes the Ile at position 276 to Pro. Oligonucleotide 875 changes Arg (275) to Leu and oligonucleotide 927 changes Phe (274) to Pro in the mutant which previously had Lys (277) converted to Leu. Thus, oligonucleotides 875 and 927 can be used to generate double mutations. Twenty pmoles of phosphorylated mutagenic primer and 20 pmoles of the second primer were combined with one pmole of single-stranded template in 10 μl of 20 mM Tris pH 7.5, 10 mM MgCl$_2$, 50 mM NaCl, 1 mM DTT and incubated at 65° C. for 10 minutes, then 5 minutes at room temperature, and placed on ice. Ten μl of 20 mM Tris pH 7.5, 10 mM MgCl$_2$, 2 mM ATP, 10 mM DTT containing 1 mM dNTPs, 2.5 units Klenow polymerase, and 3.5 units DNA ligase were added to the annealed DNA, and the mixture was incubated 3 hours at 15° C. The DNA was then transfected into competent *E. coli* JM101, and the cells were plated on YT agar and incubated at 37° C. The DNA was then transferred to nitrocellulose and prehybridized at the Tm-4° C. of the mutagenic primer for 1 hour in 6× SSC, 10× Denhardt's and hybridized to $^{32}$P-labeled mutagenic primer at Tm-4° C. in the same solution. After three washes at Tm-4° C., filters were exposed to X-ray film overnight. Additional wash steps were performed at 5° C. higher increments as necessary to identify mutant plaques. The mutated inserts were sequenced by the dideoxy method.

TABLE 4

| ZC463 | 5'CCT CAG TTT AAA ATC AAA3' |
|---|---|
| AC487 | 5'CAG CCT CAG GAG CGC ATC AAA3' |
| ZC488 | 5'CAG CCT CAA GGT CGC ATC AAA3' |
| AC489 | 5'CAG CCT CAG AGA CGC ATC AAA3' |
| AC620 | 5'CAG CCT CAG CCT CGC ATC AA3' |
| AC621 | 5'TTT CGC ATC CTC GGA GGG CTC3' |
| AC797 | 5'CTT CAG TTC GGC ATC AAA3' |
| AC814 | 5'G CCT CAG TTC GGC ATC AAA GG3' |
| AC874 | 5'CT CAG TTT CTC ATC AAA GG3' |
| AC875 | 5'CT CAG TTT CTC ATC CTC GG3' |
| AC927 | 5'CAG CCT CAG CCT CGC ATC CT3' |
| AC928 | 5'CAG TTT CGC CCC AAA GGA GG3' |
| AC1013 | 5'CT CAG TTT CCC ATC AAA GG3' |
| AZ1027 | 5'CCT CAG TTT GAC ATC AAA GG3' |

Figure 13:
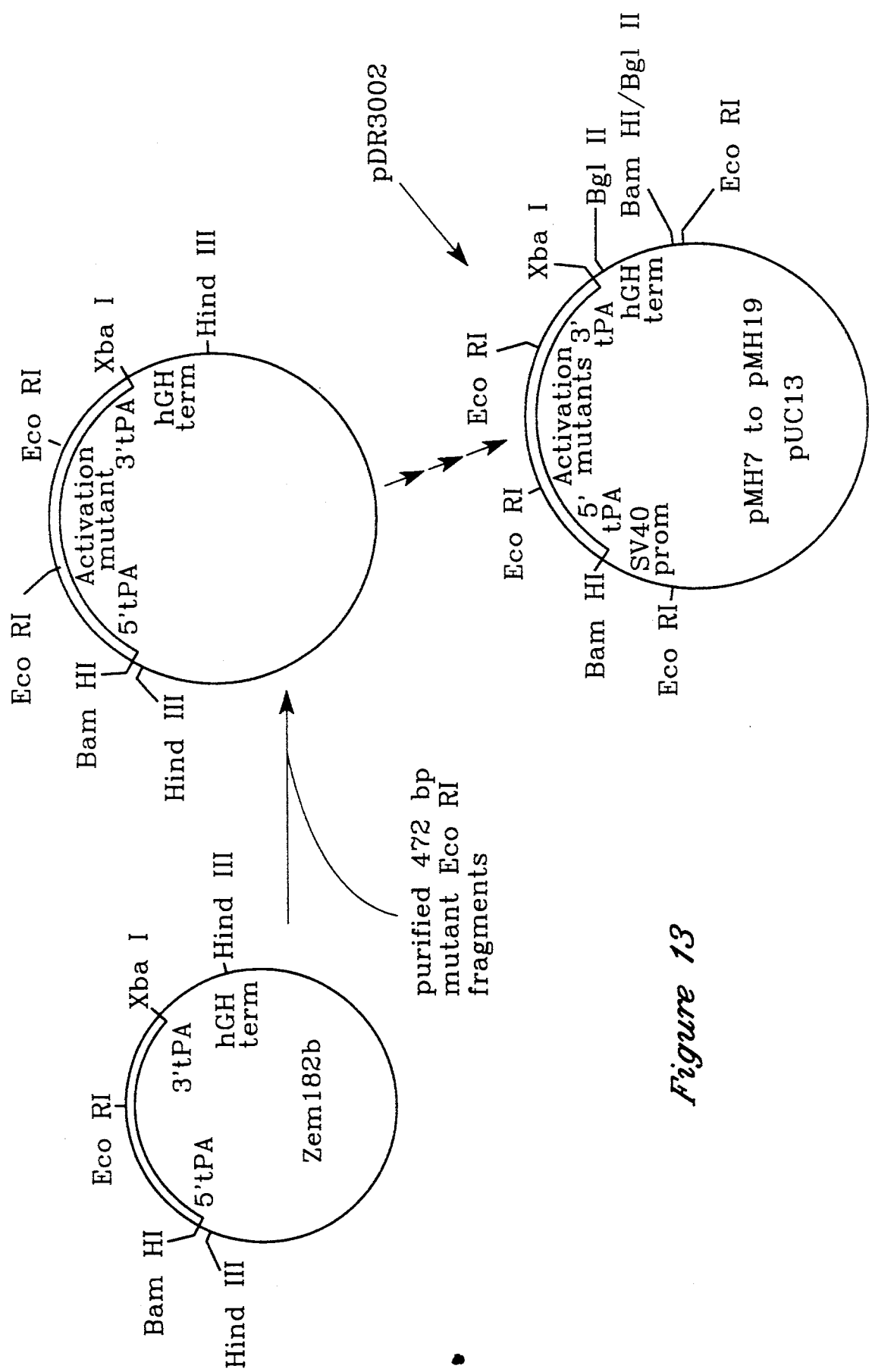
FIG. 13 illustrates the construction of the pMH series of expression vectors comprising DNA sequences encoding plasminogen activators with altered activation sites.

Expression vectors for the altered sequences were then constructed (FIG. 13). Replicative form (RF) DNA was prepared from the mutagenized phage, and the modified t-PA sequences were purified as Eco RI fragments. Plasmid Zem182b was digested with Eco RI, the vector sequences containing the 5' and 3' portions of the t-PA coding sequence were treated with calf alkaline phosphatase, and the modified t-PA sequences were inserted. The resultant plasmids were digested with Bam HI and Xba I, and the t-PA fragments were inserted into Bam HI+Xba I—cut pDR3002. The resultant vectors were designated pMH7 through pMH20 (Table 5).

TABLE 5

| Protein | Sequence of Amino Acids 273–279 |
|---|---|
| Native t-PA | Gln—Phe—Arg—Ile—Lys—Gly—Gly |
| pMH7 | Gln—Gly—Arg—Ile—Lys—Gly—Gly |
| pMH8 | Gln—Phe—Arg—Ile—Leu—Gly—Gly |
| pMH9 | Gln—Arg—Arg—Ile—Lys—Gly—Gly |
| pMH10 | Gln—Pro—Arg—Ile—Lys—Gly—Gly |
| pMH11 | Gln—Glu—Arg—Ile—Lys—Gly—Gly |
| pMH12 | Gln—Phe—Lys—Ile—Lys—Gly—Gly |
| pMH13 | Gln—Phe—Gly—Ile—Lys—Gly—Gly |
| pMH14 | Gln—Pro—Arg—Ile—Leu—Gly—Gly |
| pMH15 | Gln—Phe—Lue—Ile—Lys—Gly—Gly |
| pMH16 | Gln—Phe—Leu—Ile—Leu—Gly—Gly |
| pMH17 | Gln—Phe—Arg—Pro—Lys—Gly—Gly |
| pMH18 | Gln—Phe—Pro—Ile—Lys—Gly—Gly |
| pMH19 | Gln—Phe—Asp—Ile—Lys—Gly—Gly |
| pMH20 | Gln—Phe—Gly—Ile—Leu—Gly—Gly |

Example 7

Characterization of Representative Plasminogen Activators

Native t-PA and mutant proteins ZpL7-A, ZpL7-B and ZpL7-F (corresponding to FIG. 5A, B and F) were tested for plasma half-life in rats. For each protein tested, two female Balb/c mice weighing 20–21 grams were anesthetized with ether and injected via the tail vein with 10 μg of affinity purified protein in a total volume of 100 μl of PBS. Syringes were weighed before and after injection. At appropriate time intervals, plasma samples (25 ul) were collected from the retroorbital plexus using heparinized micropipettes. The samples were centrifuged to remove red blood cells and diluted for assay. Plasma t-PA levels were measured by ELISA using affinity purified rabbit polyclonal antibody to native human t-PA.

Figure 14:
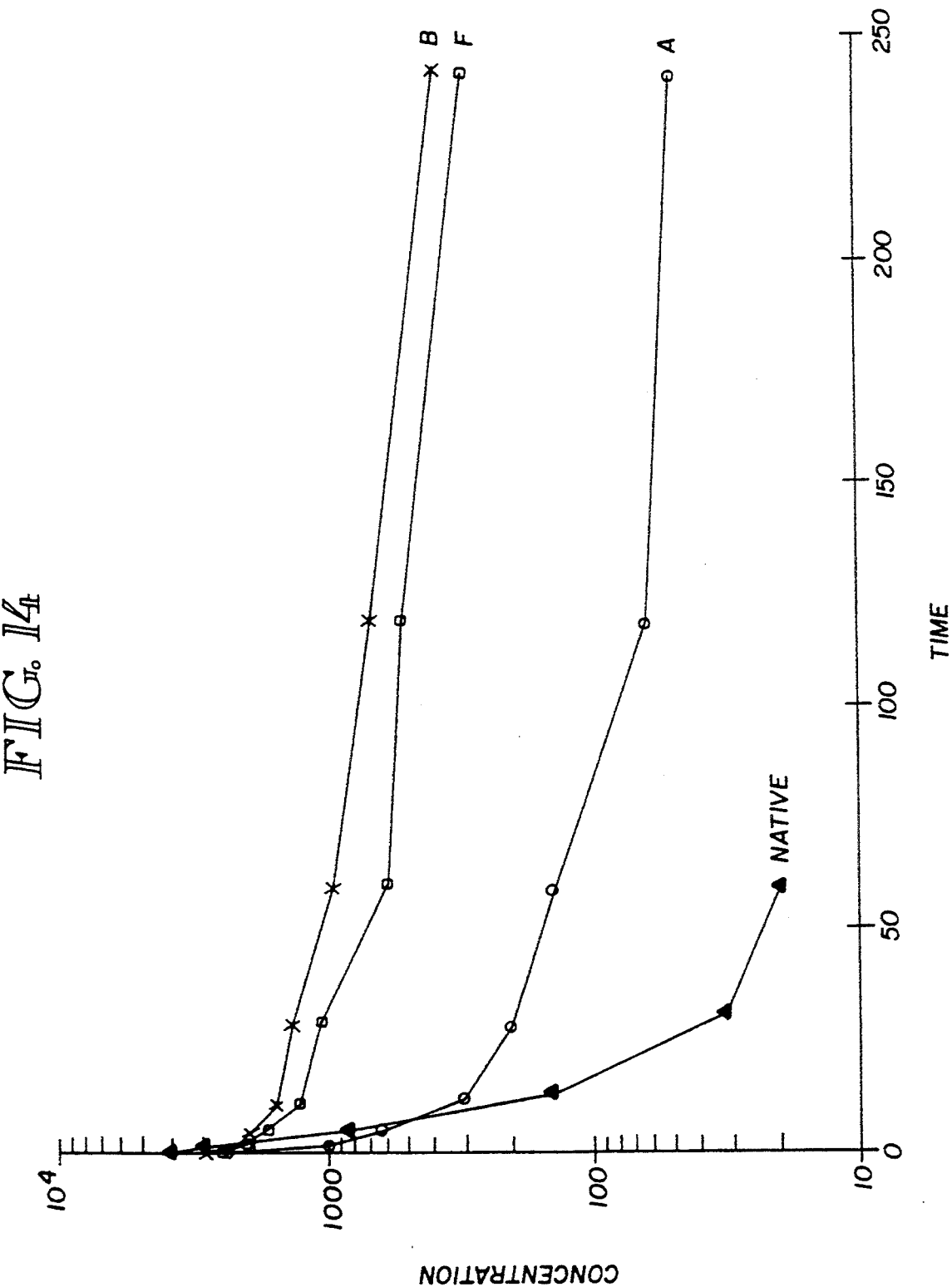
FIG. 14 shows the results of plasma half-life studies of native t-PA and three representative mutant t-PAs.

Results of the experiments are shown in FIG. 14. All three mutant proteins were found to be cleared at a significantly slower rate than native t-PA. These results suggest that the amino acid changes in the growth factor domain of analog A, and the factor IX and factor VII growth factor substitutions of analogs B and F interfere with the clearance of these molecules by the normal pathway(s).

From the foregoing, it will be appreciated that, although specific embodiments of the invention have been described herein for purposes of illustration, various modifications may be made without deviating from the spirit and scope of the invention. Accordingly, the invention is not limited except as by the appended claims.

We claim:

1. A human tissue plasminogen activator into the growth factor domain of which has been introduced a plurality of substitutions of consecutive amino acids as compared to the growth factor domain of native, human t-PA, wherein said plurality of substitutions is selected from the group consisting of fragments A-N as shown in FIG. 5, the amino acid sequences of which are encoded by the nucleotide sequences of FIG. 16, or equivalent nucleotide sequences thereto which encode said amino acid sequences.

2. The plasminogen activator of claim 1 wherein said plurality of substitutions comprises the amino acid sequence MEGNHLAN.

3. The plasminogen activator of claim 1 containing an amino acid substitution at the position corresponding to Cys (83) of native t-PA.

4. The plasminogen activator of claim 3 containing a serine residue at the position corresponding to Cys (83) of native t-PA.

5. The plasminogen activator of claim 1, wherein said plurality of substitutions contains at least one amino acid substitution between but excluding amino acid residues 62 and 73.

6. The plasminogen activator of claim 1 wherein said kringle domain is a human tissue plasminogen activator kringle domain or a human plasminogen kringle domain.

* * * * *